United States Patent [19]

Weinshank et al.

[11] Patent Number: 5,786,155
[45] Date of Patent: Jul. 28, 1998

[54] METHODS FOR IDENTIFYING A COMPOUND THAT BINDS TO A HUMAN 5-HT 1E RECEPTOR

[75] Inventors: Richard L. Weinshank, New York, N.Y.; Theresa Branchek, Teaneck; Paul R. Hartig, Mahwah, both of N.J.

[73] Assignee: Synaptic Pharmaceutical Corporation, Paramus, N.J.

[21] Appl. No.: 542,358

[22] Filed: Oct. 12, 1995

Related U.S. Application Data

[62] Division of Ser. No. 370,542, Jan. 9, 1995, Pat. No. 5,476,782, which is a continuation of Ser. No. 194,113, Feb. 8, 1994, abandoned, which is a continuation of Ser. No. 803,626, Dec. 2, 1991, abandoned.

[51] Int. Cl.$^6$ .................. G01N 33/53; G01N 33/567; G01N 33/566

[52] U.S. Cl. .................. 435/7.2; 435/7.1; 435/7.21; 436/501

[58] Field of Search .................. 435/69.1, 7.1, 435/7.2, 240.1, 240.2, 320.1, 7.21, 325, 6, 172.1, 354, 363, 356; 536/23.5; 530/350; 514/12, 21; 436/501

[56] References Cited

U.S. PATENT DOCUMENTS

| | | | |
|---|---|---|---|
| 4,675,285 | 6/1987 | Clark et al. | 435/6 |
| 4,904,582 | 2/1990 | Tullis et al. | 435/6 |
| 4,985,352 | 1/1991 | Julius et al. | 435/6 |
| 5,155,218 | 10/1992 | Weinshank et al. | 536/23.5 |
| 5,242,822 | 9/1993 | Marullo | 435/252.3 |
| 5,360,735 | 11/1994 | Weinshank et al. | 435/356 |
| 5,472,866 | 12/1995 | Gerald et al. | 435/240.2 |
| 5,476,782 | 12/1995 | Weinshank et al. | 435/240.2 |

FOREIGN PATENT DOCUMENTS

| | | |
|---|---|---|
| 2267906 | 12/1993 | United Kingdom. |
| 93/11147 | 6/1993 | WIPO. |

OTHER PUBLICATIONS

Amlaiky et al, J.Biol.Chem. 267(28): 19761–19764, 1992.
Fargin et al, Nature 335:358–360, 1988.
Levy, F.O. et al., FEBS Letters 296(3):201–206, (1992).
McAllister, G. et al., PNAS. 89:5517–5521, (1992).
Zgombick, J.M. et al., Mol. Pharm. 42:180–185, (1992).
Adham, N. et al., Neuropharmacology. 33(3/4):387–391, (1994).
Adham, N. et al., Neuropharmacology. 33(3/4):403–410, (1994).
Izant, J.G., et al., Inhibition of Thymidine Kinase Gene Expression by Antisense RNA. Cell. 1984 36:1007–1015.
Masu, Y., et al., cDNA cloning of bovine substance–K receptor. Nature. 1987 329:836–838.
Julius, D., et al., Molecular Characterization of a Functional cDNA Encoding the Serotonin 1c Receptor. Science 1988 241:558–560.
Nichols, E.K., et al., Human Gene Therapy, National Academy of Sciences, 1988 p. 118.
Leonhardt, S., et al., Detection of a Novel Serotonin Receptor Subtype (5-HT$_{1E}$) in Human Brain: Interaction with a GTP–Binding Protein. J. Neurochem., 1989 53(2):465–471.
Uhlmann, E., et al., Antisense Oligonucleotides: A New Therapeutic Principle. Chemical Reviews. 1990 90(4):544–584.
Adham, H., et al., Cloning of another human serotonin receptor (5–HT$_{1F}$): A fifth 5–HT$_1$ receptor subtype coupled to the inhibition of adenylate cyclase. PNAS 1993 90 (2):408–412.
Monsma, F.J., et al., Cloning and Expression of a Novel Serotonin Receptor with High Affinity for Tricyclic Psychotropic Drugs. Molecular Pharmacology. 1993 43(3):320–327.

Primary Examiner—Stephen Walsh
Assistant Examiner—Eliane Lazar-Wesley
Attorney, Agent, or Firm—John P. White

[57] ABSTRACT

This invention provides an isolated nucleic acid molecule encoding a human 5-HT$_{1E}$ receptor, an isolated protein which is a human 5-HT$_{1E}$ receptor, vectors comprising an isolated nucleic acid molecule encoding a human 5-HT$_{1E}$ receptors, mammalian cells comprising such vectors, antibodies directed to the human 5-HT$_{1E}$ receptor, nucleic acid probes useful for detecting nucleic acid encoding human 5-HT$_{1E}$ receptors, antisense oligonucleotides complementary to any sequences of a nucleic acid molecule which encodes a human 5-HT$_{1E}$ receptor, pharmaceutical compounds related to human 5-HT$_{1E}$ receptors, and nonhuman transgenic animals which express DNA a normal or a mutant human 5-HT$_{1E}$ receptor. This invention further provides methods for determining ligand binding, detecting expression, drug screening, and treatment involving the human 5-HT$_{1E}$ receptor.

10 Claims, 9 Drawing Sheets

FIG. 1A

```
       -730                  -710                    -690
ATATACATCATGGAATACTATGCAGCCCCCCCCAAGGATGCGTTCCATGTCCTTTGCAGG
       -670                  -650                    -630
GACATGGATGAGTTGCAAACCATATTCTCAACAAACTAACACAGCCACAGAAAACCAAAC
       -610                  -590                    -570
ACCACATGCTCTCACTCACGAGTGGAGTTGAACAATGAGAACACATGGCACAGGGCCGGG
       -550                  -530                    -510
AACATGACACACCAGGGCCTGTTGGGGGGTGGAGGGCTAGGGGAGGGATGGCATTAGGAG
       -490                  -470                    -450
AAGTACCTAATGTAGATGATTGGTTGTTGGGTGCAGCAAACCACCATGGCACATGTATAC
       -430                  -410                    -390
CTATGTAGCAAACCTGCAAGTTCTGCACATGTATCCCAGGACTTAAAGTATAATTTAAAA
       -370                  -350                    -330
AAAAACAGTTTGAAAACTTCCCTGAAGTAAAAAAAGTATCCTTTGAGGAACAATGTAACG
       -310                  -290                    -270
ATGAGCTCAAGTTCCACAGGAAAGAGAAAATTAAAATTTATAAAGAATTTATAAATATCA
       -250                  -230                    -210
AACTATTTTCATGTTTTCCAGGAAAAGTGTGGCTTTCTCATTCATTAACCAATAGCATAA
       -190                  -170                    -150
TATTTTCCAGGAACCTTCACTCAGAAGAAATGCTGTGGCCCTTCCCTTTACCAACAGAAA
       -130                  -110                    -90
ATGGAACACAAGAGACCACATAGCTGAACAAATTATAGCCTCCTTACAAGTGAGAAACCT
       -70                   -50                    -30
TCGAGGCTACATAGTTTTCAGCCAAAGGAAAATAACCAACAGCTTCTCCACAGTGTAGAC
       -10                    10                     30
```

FIG. 1B

```
TGAAACAAGGGAAACATGAACATCACAAACTGTACCACAGAGGCCAGCATGGCTATAAGA
                M  N  I  T  N  C  T  T  E  A  S  M  A  I  R
      50                   70                  90
CCCAAGACCATCACTGAGAAGATGCTCATTTGCATGACTCTGGTGGTCATCACCACCCTC
 P  K  T  I  T  E  K  M  L  I  C  M  T  L  V  V  I  T  T  L
     110                  130                 150
ACCACGTTGCTGAACTTGGCTGTGATCATGGCTATTGGCACCACCAAGAAGCTCCACCAG
 T  T  L  L  N  L  A  V  I  M  A  I  G  T  T  K  K  L  H  Q
     170                  190                 210
CCTGCCAACTACCTAATCTGTTCTCTGGCCGTGACGGACCTCCTGGTGGCAGTGCTCGTC
 P  A  N  Y  L  I  C  S  L  A  V  T  D  L  L  V  A  V  L  V
     230                  250                 270
ATGCCCCTGAGCATCATCTACATTGTCATGGATCGCTGGAAGCTTGGGTACTTCCTCTGT
 M  P  L  S  I  I  Y  I  V  M  D  R  W  K  L  G  Y  F  L  C
     290                  310                 330
GAGGTGTGGCTGAGTGTGGACATGACCTGCTGCACCTGCTCCATCCTCCACCTCTGTGTC
 E  V  W  L  S  V  D  M  T  C  C  T  C  S  I  L  H  L  C  V
     350                  370                 390
ATTGCCCTGGACAGGTACTGGGCCATCACCAATGCTATTGAATACGCCAGGAAGAGGACG
 I  A  L  D  R  Y  W  A  I  T  N  A  I  E  Y  A  R  K  R  T
     410                  430                 450
GCCAAGAGGGCCGCGCTGATGATCCTTACCGTCTGGACCATCTCCATTTTCATCTCCATG
 A  K  R  A  A  L  M  I  L  T  V  W  T  I  S  I  F  I  S  M
     470                  490                 510
CCCCCTCTGTTCTGGAGAAGCCACCGCCGCCTAAGCCCTCCCCCTAGTCAGTGCACCATC
 P  P  L  F  W  R  S  H  R  R  L  S  P  P  P  S  Q  C  T  I
     530                  550                 570
```

FIG. 1C

```
CAGCACGACCATGTTATCTACACCATTTACTCCACGCTGGGTGCGTTTTATATCCCCTTG
 Q  H  D  H  V  I  Y  T  I  Y  S  T  L  G  A  F  Y  I  P  L
         590              610              630
ACTTTGATACTGATTCTCTATTACCGGATTTACCACGCGGCCAAGAGCCTTTACCAGAAA
 T  L  I  L  I  L  Y  Y  R  I  Y  H  A  A  K  S  L  Y  Q  K
         650              670              690
AGGGGATCAAGTCGGCACTTAAGCAACAGAAGCACAGATAGCCAGAATTCTTTTGCAAGT
 R  G  S  S  R  H  L  S  N  R  S  T  D  S  Q  N  S  F  A  S
         710              730              750
TGTAAACTTACACAGACTTTCTGTGTGTCTGACTTCTCCACCTCAGACCCTACCACAGAG
 C  K  L  T  Q  T  F  C  V  S  D  F  S  T  S  D  P  T  T  E
         770              790              810
TTTGAAAAGTTCCATGCCTCCATCAGGATCCCCCCCTTCGACAATGATCTAGATCACCCA
 F  E  K  F  H  A  S  I  R  I  P  P  F  D  N  D  L  D  H  P
         830              850              870
GGAGAACGTCAGCAGATCTCTAGCACCAGGGAACGGAAGGCAGCACGCATCCTGGGGCTG
 G  E  R  Q  Q  I  S  S  T  R  E  R  K  A  A  R  I  L  G  L
         890              910              930
ATTCTGGGTGCATTCATTTTATCCTGGCTGCCATTTTTCATCAAAGAGTTGATTGTGGGT
 I  L  G  A  F  I  L  S  W  L  P  F  F  I  K  E  L  I  V  G
         950              970              990
CTGAGCATCTACACCGTGTCCTCGGAAGTGGCCGACTTTCTGACGTGGCTCGGTTATGTG
 L  S  I  Y  T  V  S  S  E  V  A  D  F  L  T  W  L  G  Y  V
        1010             1030             1050
AATTCTCTGATCAACCCTCTGCTCTATACGAGTTTTAATGAAGACTTTAAGCTGGCTTTT
 N  S  L  I  N  P  L  L  Y  T  S  F  N  E  D  F  K  L  A  F
```

FIG. 1D

```
1070                1090                1110
AAAAAGCTCATTAGATGCCGAGAGCATACTTAGACTGTAAAAAGCTAAAAGGCACGACTT
  K   K   L   I   R   C   R   E   H   T
     1130                1150                1170
TTTCCAGAGCCTCATGAGTGGATGGGGGTAAGGGGTGCAACTTATTAATTCTTGAACATA
     1190                1210                1230
CTTGGTTCAGGAGAGTTTGTAAGTATGTGTGGTCTTGTTTCCTTGTTTGTTTGTTTGTTT
     1250                1270                1290
TGTTCTGTTTTGTTTGAGGATTGTTATTTGGCCTCCTGTTTTCTACCTCTGGTCTTATCT
     1310                1330                1350
GTGATACATAATTTCAAATAAACATTATCATACAAAAACAGAAATTTTGCCAGAAGTAAT
     1370                1390                1410
AATAAGATGAAATACTAAATACCTTTTATGGGTTTTTTTTTTTAGCCATTTCAGTTACC
     1430                1450                1470
CTGCAATTAAAGAATGCCAAAAATATCTTTATTTGCAGAATTTCTTATTACTTATAAATT
     1490                1510                1530
AAATACCTGATAATGCCCTCCATGGCATTAAATCTGAGATTATGGCTCTATCTGCGTACA
     1550                1570                1590
TATTCCAGTGGGAATTGCATGACTACATAAAGAATTAAAAGAAAGTGATGTGCTGTCATC
     1610                1630                1650
TACGGCTTGCGACCTGAGCTAAAGTCGGGGGCTGTAGCACTGTGACTACGTAGCCTATCA
     1670                1690                1710
TTTCAGGTAAAAATAGTACAGCTGGCTTGTCTTGTTAGTTCATGATTAAATAAACTTCTC

TTT
```

FIG. 2A

```
                    1                                                              50
       5HT1C        M..........  ...........  ...VNLGNAV  RSLLMHLIGL  LVWQFDISIS
       5HT2         MDILCEENTS   LSSTTNSLMQ   LNDDTRLYSN  DFNSGEANTS  DAFNWTVDSE
       5HT1Dα       M..........  ...........  ...........  ......SPLN  QSAEGLPQEA
       5HT1Dβ       M..........  ...........  .........EE  PGAQCAPPAP  AGSETWVPQA
       5HT1E        M..........  ...........  ...........  ...........  ...........
       5HT1A        M..........  ...........  ...........  ...........  .DVLSPGQGN
TM Region           ...........  ...........  ...........  ...........  ...........

51                                                             100
       5HT1C        PVAAIVTDTF   NSSDGGRLFQ   FPDGVQNWPA  LSIVVIIIMT  IGGNILVIMA
       5HT2         NRTNLSCEGC   LSPSCLSLLH   LQE..KNWSA  LLTAVVIILT  IAGNILVIMA
       5HT1Dα       ...SNRSLNA   TETSEAWDPR   TLQALKISLP  VLLSVITLAT  VLSNAFVLTT
       5HT1Dβ       NLSSAPSQNC   SAKDYIYQDS   ISLPWKVLLV  MLLALITLAT  TLSNAFVIAT
       5HT1E        .....NITNC   TTEASMAIRP   KTITEKMLIC  MTLVVITTLT  TLLNLAVIMA
       5HT1A        NTTSPPAPFE   TGGNTTGISD   VTVSYQVITS  LLLGTLIFCA  VLGNACVVAA
TM Region           ...........  ...........  .....****   ********..  I..*******

101                                                            150
       5HT1C        VSMEKKLHNA   TNYFLMSLAI   ADMLVGLLVM  PLSLLAILYD  YVWPLPRYLC
       5HT2         VSLEKKLQNA   TNYFLMSLAI   ADMLLGFLVM  PVSMLTILYG  YRWPLPSKLC
       5HT1Dα       ILLTRKLHTP   ANYLIGSLAT   TDLLVSILVM  PISMAYTITH  .TWNFGQILC
       5HT1Dβ       VYRTRKLHTP   ANYLIASLDV   TDLLVSILVI  PISTMYTVTD  .RWTLSQVVC
       5HT1E        IGTTKKLHQP   ANYLICSLAV   TDLLVAVLVM  PLSIIYIVMD  .RWKLGYFLC
       5HT1A        IALERSLQNV   ANYLIGSLAV   TDLMVSVLVL  PMAALYQVLN  .KWTLGQVTC
TM Region           *..........  ...*******   ***..II..*  ********..  ...........

151                                                            200
       5HT1C        PVWISLDVLF   STASIMHLCA   ISLDRYVAIR  NPIEHSRFNS  RTKAIMKIAI
       5HT2         AVWIYLDVLF   STASIMHLCA   ISLDRYVAIQ  NPIHHSRFNS  RTKAFLKIIA
       5HT1Dα       DIWLSSDITC   CTASILHLCV   IALDRYWAIT  DALEYSKRRT  AGHAATMIAI
       5HT1Dβ       DFWLSSDITC   CTASILHLCV   IALDRYWAIT  DAVEYSAKRT  PKRAAVMIAL
       5HT1E        EVWLSVDMTC   CTCSILHLCV   IALDRYWAIT  NAIEYARKRT  AKRAALMILT
       5HT1A        DLFIALDVLC   CTSSILHLCA   IALDRYWAIT  DPIDYVNKRT  PRRAAALISL
TM Region           .*******.   .III..****   ***.......  ...........  ......****

201                                                            250
       5HT1C        VWAISIGVSV   PIPVIGLRDE   SKVFVNNTTC  VLNDPNFVLI  GSFVAFFIPL
       5HT2         VWTISVGISM   PIPVFGLQDD   SKVF.KEGSC  LLADDNFVLI  GSFVSFFIPL
       5HT1Dα       VWAISICISI   PPLFWR.QEK   AQEEMSDCLV  NTSQISYTIY  STCGAFYIPS
       5HT1Dβ       VWVFSISISL   PPFFWR.QAK   AEEEVSECVV  NTDHILYTVY  STVGAFYFPT
       5HT1E        VWTISIFISM   PPLFWRSHRR   LSPPPSQCTI  QHDHVIYTIY  STLGAFYIPL
       5HT1A        TWLIGFLISI   PPMLGWRTPE   DRSDPDACTI  SKDH.GYTIY  STFGAFYIPL
TM Region           ****..IV..   ********..   ...........  ......****  *****..V..

251                                                            300
       5HT1C        TIMVITY...   ...........  ...........  ...........  ...........
       5HT2         TIMVITY...   ...........  ...........  ...........  ...........
       5HT1Dα       VLLIILYGRI   YRAAR......  ...........  ...........  ...........
       5HT1Dβ       LLLIALYGRI   YVEAR......  ...........  ...........  ...........
       5HT1E        TLILILYYRI   YHAAKSLYQK   R..........  ...........  ...........
       5HT1A        LLMLVLYGRI   FRAARFRIRK   TVKKVEKTGA  DTRHGASPAP  QPKKSVNGES
TM Region           *******...   ...........  ...........  ...........  ...........
```

FIG. 2B

```
              301                                                          350
  5HT1C       .....FLTIY  VLRRQTLMLL  RG.HTEEELA  NMSLNFLNCC  CKKNGGEEEN
  5HT2        .....FLTIK  SLQKEATLCV  SDLGTRAKLA  ..SFSFLPQS  SLSSEKLFQR
  5HT1Dα      ...NRIL.NP  PSLSGKRFTT  AHLITGSAG.  ...SVCSL...  ..NSSLHEGH
  5HT1Dβ      ...SRILKQT  PNRTGKRLTR  AQLITDSPGS  TSSVTSI...  ..NSRVPDVP
  5HT1E       .GSSRHLSNR  STDSQNSFAS  CKLTQTFCVS  DFSTSDP...  ..TTEFEKFH
  5HT1A       GSRNWRLGVE  SKAGGALCAN  GAVRQGDDGA  ALEVIEVHRV  GNSKEHLPLP
TM Region     ..........  ..........  ..........  ..........  ..........

351                                                          400
  5HT1C       APNPNPDQKP  RR...KKKEK  RPRGTMQAIN  NEKKASKVLG  IVFFVFLIMW
  5HT2        SIHREPGSYT  GR...R....  ....TMQSIS  NEQKACKVLG  IVFFLFVVMW
  5HT1Dα      SHSAGSPLFF  NHVKIKLADS  ALERKRISAA  RERKATKILG  IILGAFIICW
  5HT1Dβ      SES.GSPVYV  NQVKVRVSDA  LLEKKKLMAA  RERKATKTLG  IILGAFIVCW
  5HT1E       A.SIRIPPFD  NDL.....DH  PGERQQISST  RERKAARILG  LILGAFILSW
  5HT1A       SEAGPTPCAP  ASFERKNERN  AEAKRKMALA  RERKTVKTLG  IIMGTFILCW
TM Region     ..........  ..........  ..........  ........  *****..V 401                                                          450
  5HT1C       CPFFITNILS  VLCGKACNQK  LMEKLLNVFV  WIGYVCSGIN  PLVYTLFNKI
  5HT2        CPFFITNIMA  VICKESCNED  VIGALLNVFV  WIGYLSSAVN  PLVYTLFNKT
  5HT1Dα      LPFFVVSLVL  PICRDSCWIH  P..GLFDFFT  WLGYLNSLIN  PIIYTVFNEE
  5HT1Dβ      LPFFIISLVM  PICKDACWFH  L..AIFDFFT  WLGYLNSLIN  PIIYTMSNED
  5HT1E       LPFFIKELIV  GLSIYTVSSE  V..A..DFLT  WLGYVNSLIN  PLLYTSFNED
  5HT1A       LPFFIVALVL  PFCESSCHMP  T..LLGAIIN  WLGYSNSLLN  PVIYAYFNKD
TM Region     I..*******  *.........  ..*******.  **..VII..*  *******...

451                                                          500
  5HT1C       YRRAFSKYLR  CDYKPDKKP.  PVRQIPRVAA  TALSGRELNV  NIYRHTNERV
  5HT2        YRSAFSRYIQ  CQYKENKKPL  QLILVNTIPA  LAYKSSQLQM  GQKKNSKQDA
  5HT1Dα      FRQAFQKIVP  FRKA......  ..........  ..........  ..........
  5HT1Dβ      FKQAFHKLIR  LSAQVDLPFA  VGP.......  ..........  ..........
  5HT1E       FKLAFKKLIR  CREHT.....  ..........  ..........  ..........
  5HT1A       FQNAFKKIIK  CLFCRQ*...  ..........  ..........  ..........
TM Region     ..........  ..........  ..........  ..........  ..........

501                                    536
  5HT1C       ARKANDPEPG  IEMQVENLEL  PVNPSNVVSE  RISSV*
  5HT2        KTTDNDCSMV  ALGKQHSEEA  SKDNSDGVNE  KVSCV*
  5HT1Dα      ..........  ..........  ..........  ......
  5HT1Dβ      ..........  ..........  ..........  ......
  5HT1E       ..........  ..........  ..........  ......
  5HT1A       ..........  ..........  ..........  ......
TM Region     ..........  ..........  ..........  ......
```

FIG. 5

| Brain Tissues | 5-HT$_{1E}$ | | |
|---|---|---|---|
| | Experiment 1 | Experiment 2 | Experiment 3 |
| Frontal Cortex | + | + | + |
| Cerebellar Cortex | + + | + | + + |
| Temporal Cortex | + | + + | + + + |
| Choroid Plexus | + + + | + + | + + + |
| Hippocampus | + + + | + + | + + + |
| Brain Stem | + | + + | + + + |
| Cortex | + + | + + | + + + |
| (+) Control | + + + | + + + | + + + |
| (-) Control | - | - | - |

Figure Key:
+ + + = dark
+ + = light
+ = present but faint
- = absent

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2463 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i i ) IMMEDIATE SOURCE:
        ( A ) LIBRARY: human placental genomic
        ( B ) CLONE: hp75d ( v i i i ) POSITION IN GENOME:
        ( C ) UNITS: bp ( i x ) FEATURE:
        ( A ) NAME/KEY: CDS
        ( B ) LOCATION: 736..1830

( i x ) FEATURE:
        ( A ) NAME/KEY: mat_peptide
        ( B ) LOCATION: 736..1830

( x i ) SEQUENCE DESCRIPTION: SEQ ID NO:1:

```
ATATACATCA TGGAATACTA TGCAGCCCCC CCCAAGGATG CGTTCCATGT CCTTTGCAGG      60

GACATGGATG AGTTGCAAAC CATATTCTCA ACAAACTAAC ACAGCCACAG AAAACCAAAC     120

ACCACATGCT CTCACTCACG AGTGGAGTTG AACAATGAGA ACACATGGCA CAGGGCCGGG     180

AACATGACAC ACCAGGGCCT GTTGGGGGGT GGAGGGCTAG GGGAGGGATG GCATTAGGAG     240

AAGTACCTAA TGTAGATGAT TGGTTGTTGG GTGCAGCAAA CCACCATGGC ACATGTATAC     300

CTATGTAGCA AACCTGCAAG TTCTGCACAT GTATCCCAGG ACTTAAAGTA TAATTTAAAA     360
```

-continued

```
AAAAACAGTT TGAAAACTTC CCTGAAGTAA AAAAAGTATC CTTTGAGGAA CAATGTAACG        420

ATGAGCTCAA GTTCCACAGG AAAGAGAAAA TTAAATTTA TAAAGAATTT ATAAATATCA         480

AACTATTTTC ATGTTTTCCA GGAAAAGTGT GGCTTTCTCA TTCATTAACC AATAGCATAA        540

TATTTTCCAG GAACCTTCAC TCAGAAGAAA TGCTGTGGCC CTTCCCTTTA CCAACAGAAA        600

ATGGAACACA AGAGACCACA TAGCTGAACA AATTATAGCC TCCTTACAAG TGAGAAACCT        660

TCGAGGCTAC ATAGTTTTCA GCCAAGGGAA AATAACCAAC AGCTTCTCCA CAGTGTAGAC        720

TGAAACAAGG GAAAC ATG AAC ATC ACA AAC TGT ACC ACA GAG GCC AGC ATG        771
              Met Asn Ile Thr Asn Cys Thr Thr Glu Ala Ser Met
                1              5                  10

GCT ATA AGA CCC AAG ACC ATC ACT GAG AAG ATG CTC ATT TGC ATG ACT         819
Ala Ile Arg Pro Lys Thr Ile Thr Glu Lys Met Leu Ile Cys Met Thr
              15              20                  25

CTG GTG GTC ATC ACC ACC CTC ACC ACG TTG CTG AAC TTG GCT GTG ATC         867
Leu Val Val Ile Thr Thr Leu Thr Thr Leu Leu Asn Leu Ala Val Ile
        30              35                  40

ATG GCT ATT GGC ACC ACC AAG AAG CTC CAC CAG CCT GCC AAC TAC CTA         915
Met Ala Ile Gly Thr Thr Lys Lys Leu His Gln Pro Ala Asn Tyr Leu
45              50                  55                      60

ATC TGT TCT CTG GCC GTG ACG GAC CTC CTG GTG GCA GTG CTC GTC ATG         963
Ile Cys Ser Leu Ala Val Thr Asp Leu Leu Val Ala Val Leu Val Met
                65                  70                      75

CCC CTG AGC ATC ATC TAC ATT GTC ATG GAT CGC TGG AAG CTT GGG TAC        1011
Pro Leu Ser Ile Ile Tyr Ile Val Met Asp Arg Trp Lys Leu Gly Tyr
            80                  85                  90

TTC CTC TGT GAG GTG TGG CTG AGT GTG GAC ATG ACC TGC TGC ACC TGC        1059
Phe Leu Cys Glu Val Trp Leu Ser Val Asp Met Thr Cys Cys Thr Cys
            95                  100                 105

TCC ATC CTC CAC CTC TGT GTC ATT GCC CTG GAC AGG TAC TGG GCC ATC        1107
Ser Ile Leu His Leu Cys Val Ile Ala Leu Asp Arg Tyr Trp Ala Ile
110                 115                 120

ACC AAT GCT ATT GAA TAC GCC AGG AAG AGG ACG GCC AAG AGG GCC GCG        1155
Thr Asn Ala Ile Glu Tyr Ala Arg Lys Arg Thr Ala Lys Arg Ala Ala
125                 130                 135                 140

CTG ATG ATC CTT ACC GTC TGG ACC ATC TCC ATT TTC ATC TCC ATG CCC        1203
Leu Met Ile Leu Thr Val Trp Thr Ile Ser Ile Phe Ile Ser Met Pro
                145                 150                 155

CCT CTG TTC TGG AGA AGC CAC CGC CGC CTA AGC CCT CCC CCT AGT CAG        1251
Pro Leu Phe Trp Arg Ser His Arg Arg Leu Ser Pro Pro Pro Ser Gln
            160                 165                 170

TGC ACC ATC CAG CAC GAC CAT GTT ATC TAC ACC ATT TAC TCC ACG CTG        1299
Cys Thr Ile Gln His Asp His Val Ile Tyr Thr Ile Tyr Ser Thr Leu
        175                 180                 185

GGT GCG TTT TAT ATC CCC TTG ACT TTG ATA CTG ATT CTC TAT TAC CGG        1347
Gly Ala Phe Tyr Ile Pro Leu Thr Leu Ile Leu Ile Leu Tyr Tyr Arg
190                 195                 200

ATT TAC CAC GCG GCC AAG AGC CTT TAC CAG AAA AGG GGA TCA AGT CGG        1395
Ile Tyr His Ala Ala Lys Ser Leu Tyr Gln Lys Arg Gly Ser Ser Arg
205                 210                 215                 220

CAC TTA AGC AAC AGA AGC ACA GAT AGC CAG AAT TCT TTT GCA AGT TGT        1443
His Leu Ser Asn Arg Ser Thr Asp Ser Gln Asn Ser Phe Ala Ser Cys
                225                 230                 235

AAA CTT ACA CAG ACT TTC TGT GTG TCT GAC TTC TCC ACC TCA GAC CCT        1491
Lys Leu Thr Gln Thr Phe Cys Val Ser Asp Phe Ser Thr Ser Asp Pro
            240                 245                 250

ACC ACA GAG TTT GAA AAG TTC CAT GCC TCC ATC AGG ATC CCC CCC TTC        1539
Thr Thr Glu Phe Glu Lys Phe His Ala Ser Ile Arg Ile Pro Pro Phe
        255                 260                 265
```

| | | | | | | | | | | | | | | | | |
|---|---|---|---|---|---|---|---|---|---|---|---|---|---|---|---|---|
| GAC | AAT | GAT | CTA | GAT | CAC | CCA | GGA | GAA | CGT | CAG | CAG | ATC | TCT | AGC | ACC | 1587 |
| Asp | Asn | Asp | Leu | Asp | His | Pro | Gly | Glu | Arg | Gln | Gln | Ile | Ser | Ser | Thr | |
| | 270 | | | | 275 | | | | | 280 | | | | | | |
| AGG | GAA | CGG | AAG | GCA | GCA | CGC | ATC | CTG | GGG | CTG | ATT | CTG | GGT | GCA | TTC | 1635 |
| Arg | Glu | Arg | Lys | Ala | Ala | Arg | Ile | Leu | Gly | Leu | Ile | Leu | Gly | Ala | Phe | |
| 285 | | | | 290 | | | | | 295 | | | | | 300 | | |
| ATT | TTA | TCC | TGG | CTG | CCA | TTT | TTC | ATC | AAA | GAG | TTG | ATT | GTG | GGT | CTG | 1683 |
| Ile | Leu | Ser | Trp | Leu | Pro | Phe | Phe | Ile | Lys | Glu | Leu | Ile | Val | Gly | Leu | |
| | | | | 305 | | | | | 310 | | | | | 315 | | |
| AGC | ATC | TAC | ACC | GTG | TCC | TCG | GAA | GTG | GCC | GAC | TTT | CTG | ACG | TGG | CTC | 1731 |
| Ser | Ile | Tyr | Thr | Val | Ser | Ser | Glu | Val | Ala | Asp | Phe | Leu | Thr | Trp | Leu | |
| | | | 320 | | | | | 325 | | | | | 330 | | | |
| GGT | TAT | GTG | AAT | TCT | CTG | ATC | AAC | CCT | CTG | CTC | TAT | ACG | AGT | TTT | AAT | 1779 |
| Gly | Tyr | Val | Asn | Ser | Leu | Ile | Asn | Pro | Leu | Leu | Tyr | Thr | Ser | Phe | Asn | |
| | | 335 | | | | | 340 | | | | | 345 | | | | |
| GAA | GAC | TTT | AAG | CTG | GCT | TTT | AAA | AAG | CTC | ATT | AGA | TGC | CGA | GAG | CAT | 1827 |
| Glu | Asp | Phe | Lys | Leu | Ala | Phe | Lys | Lys | Leu | Ile | Arg | Cys | Arg | Glu | His | |
| | 350 | | | | | 355 | | | | | 360 | | | | | |
| ACT | TAGACTGTAA | AAAGCTAAAA | GGCACGACTT | TTTCCAGAGC | CTCATGAGTG | | | | | | | | | | | 1880 |
| Thr | | | | | | | | | | | | | | | | |
| 365 | | | | | | | | | | | | | | | | |

```
GATGGGGGTA AGGGGTGCAA CTTATTAATT CTTGAACATA CTTGGTTCAG GAGAGTTTGT    1940
AAGTATGTGT GGTCTTGTTT CCTTGTTTGT TTGTTTGTTT TGTTCTGTTT TGTTTGAGGA    2000
TTGTTATTTG GCCTCCTGTT TTCTACCTCT GGTCTTATCT GTGATACATA ATTTCAAATA    2060
AACATTATCA TACAAAAACA GAAATTTTGC CAGAAGTAAT AATAAGATGA AATACTAAAT    2120
ACCTTTTATG GGTTTTTTTT TTTTAGCCAT TCAGTTACC  CTGCAATTAA AGAATGCCAA    2180
AAATATCTTT ATTTGCAGAA TTTCTTATTA CTTATAAATT AAATACCTGA TAATGCCCTC    2240
CATGGCATTA AATCTGAGAT TATGGCTCTA TCTGCGTACA TATTCCAGTG GGAATTGCAT    2300
GACTACATAA AGAATTAAAA GAAAGTGATG TGCTGTCATC TACGGCTTGC GACCTGAGCT    2360
AAAGTCGGGG GCTGTAGCAC TGTGACTACG TAGCCTATCA TTTCAGGTAA AAATAGTACA    2420
GCTGGCTTGT CTTGTTAGTT CATGATTAAA TAAACTTCTC TTT                      2463
```

(2) INFORMATION FOR SEQ ID NO:2:

(i) SEQUENCE CHARACTERISTICS:
    (A) LENGTH: 365 amino acids
    (B) TYPE: amino acid
    (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Asn | Ile | Thr | Asn | Cys | Thr | Thr | Glu | Ala | Ser | Met | Ala | Ile | Arg | Pro |
| 1 | | | | 5 | | | | 10 | | | | | 15 | | |
| Lys | Thr | Ile | Thr | Glu | Lys | Met | Leu | Ile | Cys | Met | Thr | Leu | Val | Val | Ile |
| | | | 20 | | | | 25 | | | | | 30 | | | |
| Thr | Thr | Leu | Thr | Thr | Leu | Leu | Asn | Leu | Ala | Val | Ile | Met | Ala | Ile | Gly |
| | | | 35 | | | | 40 | | | | | 45 | | | |
| Thr | Thr | Lys | Lys | Leu | His | Gln | Pro | Ala | Asn | Tyr | Leu | Ile | Cys | Ser | Leu |
| | 50 | | | | 55 | | | | 60 | | | | | | |
| Ala | Val | Thr | Asp | Leu | Leu | Val | Ala | Val | Leu | Val | Met | Pro | Leu | Ser | Ile |
| 65 | | | | 70 | | | | 75 | | | | | | | 80 |
| Ile | Tyr | Ile | Val | Met | Asp | Arg | Trp | Lys | Leu | Gly | Tyr | Phe | Leu | Cys | Glu |
| | | | | 85 | | | | 90 | | | | | 95 | | |
| Val | Trp | Leu | Ser | Val | Asp | Met | Thr | Cys | Cys | Thr | Cys | Ser | Ile | Leu | His |
| | | | 100 | | | | 105 | | | | | 110 | | | |

```
Leu Cys Val Ile Ala Leu Asp Arg Tyr Trp Ala Ile Thr Asn Ala Ile
        115             120                 125
Glu Tyr Ala Arg Lys Arg Thr Ala Lys Arg Ala Ala Leu Met Ile Leu
    130             135             140
Thr Val Trp Thr Ile Ser Ile Phe Ile Ser Met Pro Pro Leu Phe Trp
145             150             155                         160
Arg Ser His Arg Arg Leu Ser Pro Pro Ser Gln Cys Thr Ile Gln
                165         170                     175
His Asp His Val Ile Tyr Thr Ile Tyr Ser Thr Leu Gly Ala Phe Tyr
            180             185                 190
Ile Pro Leu Thr Leu Ile Leu Ile Leu Tyr Tyr Arg Ile Tyr His Ala
        195             200             205
Ala Lys Ser Leu Tyr Gln Lys Arg Gly Ser Ser Arg His Leu Ser Asn
    210             215             220
Arg Ser Thr Asp Ser Gln Asn Ser Phe Ala Ser Cys Lys Leu Thr Gln
225             230             235                         240
Thr Phe Cys Val Ser Asp Phe Ser Thr Ser Asp Pro Thr Thr Glu Phe
                245             250                     255
Glu Lys Phe His Ala Ser Ile Arg Ile Pro Pro Phe Asp Asn Asp Leu
            260             265             270
Asp His Pro Gly Glu Arg Gln Gln Ile Ser Ser Thr Arg Glu Arg Lys
        275             280             285
Ala Ala Arg Ile Leu Gly Leu Ile Leu Gly Ala Phe Ile Leu Ser Trp
    290             295             300
Leu Pro Phe Phe Ile Lys Glu Leu Ile Val Gly Leu Ser Ile Tyr Thr
305             310             315                         320
Val Ser Ser Glu Val Ala Asp Phe Leu Thr Trp Leu Gly Tyr Val Asn
                325             330                     335
Ser Leu Ile Asn Pro Leu Leu Tyr Thr Ser Phe Asn Glu Asp Phe Lys
            340             345             350
Leu Ala Phe Lys Lys Leu Ile Arg Cys Arg Glu His Thr
        355             360             365
```

( 2 ) INFORMATION FOR SEQ ID NO:3:

( i ) SEQUENCE CHARACTERISTICS:
      ( A ) LENGTH: 422 amino acids
      ( B ) TYPE: amino acid
      ( C ) STRANDEDNESS: unknown
      ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
Met Asp Val Leu Ser Pro Gly Gln Gly Asn Asn Thr Thr Ser Pro Pro
1               5                   10                      15
Ala Pro Phe Glu Thr Gly Gly Asn Thr Thr Gly Ile Ser Asp Val Thr
            20              25                  30
Val Ser Tyr Gln Val Ile Thr Ser Leu Leu Leu Gly Thr Leu Ile Phe
        35              40                  45
Cys Ala Val Leu Gly Asn Ala Cys Val Val Ala Ala Ile Ala Leu Glu
    50              55                  60
```

```
Arg  Ser  Leu  Gln  Asn  Val  Ala  Asn  Tyr  Leu  Ile  Gly  Ser  Leu  Ala  Val
 65                  70                  75                  80

Thr  Asp  Leu  Met  Val  Ser  Val  Leu  Val  Leu  Pro  Met  Ala  Ala  Leu  Tyr
                    85                  90                  95

Gln  Val  Leu  Asn  Lys  Trp  Thr  Leu  Gly  Gln  Val  Thr  Cys  Asp  Leu  Phe
               100                 105                 110

Ile  Ala  Leu  Asp  Val  Leu  Cys  Cys  Thr  Ser  Ser  Ile  Leu  His  Leu  Cys
               115                 120                 125

Ala  Ile  Ala  Leu  Asp  Arg  Tyr  Trp  Ala  Ile  Thr  Asp  Pro  Ile  Asp  Tyr
     130                 135                 140

Val  Asn  Lys  Arg  Thr  Pro  Arg  Arg  Ala  Ala  Ala  Leu  Ile  Ser  Leu  Thr
145                      150                 155                      160

Trp  Leu  Ile  Gly  Phe  Leu  Ile  Ser  Ile  Pro  Pro  Met  Leu  Gly  Trp  Arg
                    165                 170                      175

Thr  Pro  Glu  Asp  Arg  Ser  Asp  Pro  Asp  Ala  Cys  Thr  Ile  Ser  Lys  Asp
               180                 185                 190

His  Gly  Tyr  Thr  Ile  Tyr  Ser  Thr  Phe  Gly  Ala  Phe  Tyr  Ile  Pro  Leu
          195                      200                 205

Leu  Leu  Met  Leu  Val  Leu  Tyr  Gly  Arg  Ile  Phe  Arg  Ala  Ala  Arg  Phe
     210                      215                 220

Arg  Ile  Arg  Lys  Thr  Val  Lys  Lys  Val  Glu  Lys  Thr  Gly  Ala  Asp  Thr
225                      230                 235                      240

Arg  His  Gly  Ala  Ser  Pro  Ala  Pro  Gln  Pro  Lys  Lys  Ser  Val  Asn  Gly
                    245                 250                      255

Glu  Ser  Gly  Ser  Arg  Asn  Trp  Arg  Leu  Gly  Val  Glu  Ser  Lys  Ala  Gly
               260                 265                 270

Gly  Ala  Leu  Cys  Ala  Asn  Gly  Ala  Val  Arg  Gln  Gly  Asp  Asp  Gly  Ala
          275                 280                 285

Ala  Leu  Glu  Val  Ile  Glu  Val  His  Arg  Val  Gly  Asn  Ser  Lys  Glu  His
     290                      295                 300

Leu  Pro  Leu  Pro  Ser  Glu  Ala  Gly  Pro  Thr  Pro  Cys  Ala  Pro  Ala  Ser
305                      310                 315                      320

Phe  Glu  Arg  Lys  Asn  Glu  Arg  Asn  Ala  Glu  Ala  Lys  Arg  Lys  Met  Ala
                    325                 330                      335

Leu  Ala  Arg  Glu  Arg  Lys  Thr  Val  Lys  Thr  Leu  Gly  Ile  Ile  Met  Gly
               340                 345                 350

Thr  Phe  Ile  Leu  Cys  Trp  Leu  Pro  Phe  Phe  Ile  Val  Ala  Leu  Val  Leu
          355                 360                 365

Pro  Phe  Cys  Glu  Ser  Ser  Cys  His  Met  Pro  Thr  Leu  Leu  Gly  Ala  Ile
370                      375                 380

Ile  Asn  Trp  Leu  Gly  Tyr  Ser  Asn  Ser  Leu  Leu  Asn  Pro  Val  Ile  Tyr
385                      390                 395                      400

Ala  Tyr  Phe  Asn  Lys  Asp  Phe  Gln  Asn  Ala  Phe  Lys  Lys  Ile  Ile  Lys
                    405                 410                      415

Cys  Leu  Phe  Cys  Arg  Gln
                    420
```

( 2 ) INFORMATION FOR SEQ ID NO:4:

( i ) SEQUENCE CHARACTERISTICS:
  ( A ) LENGTH: 460 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Met Val Asn Leu Gly Asn Ala Val Arg Ser Leu Leu Met His Leu Ile
 1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
         35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Ile Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Ala Asn Met Ser Leu Asn Phe Leu Asn Cys Cys Cys Lys Lys
            260                 265                 270

Asn Gly Gly Glu Glu Glu Asn Ala Pro Asn Pro Asn Pro Asp Gln Lys
        275                 280                 285

Pro Arg Arg Lys Lys Lys Glu Lys Arg Pro Arg Gly Thr Met Gln Ala
    290                 295                 300

Ile Asn Asn Glu Lys Lys Ala Ser Lys Val Leu Gly Ile Val Phe Phe
305                 310                 315                 320

Val Phe Leu Ile Met Trp Cys Pro Phe Phe Ile Thr Asn Ile Leu Ser
                325                 330                 335

Val Leu Cys Gly Lys Ala Cys Asn Gln Lys Leu Met Glu Lys Leu Leu
            340                 345                 350

Asn Val Phe Val Trp Ile Gly Tyr Val Cys Ser Gly Ile Asn Pro Leu
        355                 360                 365

Val Tyr Thr Leu Phe Asn Lys Ile Tyr Arg Arg Ala Phe Ser Lys Tyr
    370                 375                 380
```

```
Leu  Arg  Cys  Asp  Tyr  Lys  Pro  Asp  Lys  Lys  Pro  Pro  Val  Arg  Gln  Ile
385                 390                 395                                400

Pro  Arg  Val  Ala  Ala  Thr  Ala  Leu  Ser  Gly  Arg  Glu  Leu  Asn  Val  Asn
                    405                      410                      415

Ile  Tyr  Arg  His  Thr  Asn  Glu  Arg  Val  Ala  Arg  Lys  Ala  Asn  Asp  Pro
               420                      425                      430

Glu  Pro  Gly  Ile  Glu  Met  Gln  Val  Glu  Asn  Leu  Glu  Leu  Pro  Val  Asn
          435                      440                      445

Pro  Ser  Asn  Val  Val  Ser  Glu  Arg  Ile  Ser  Ser  Val
          450                 455                 460
```

( 2 ) INFORMATION FOR SEQ ID NO:5:

( i ) SEQUENCE CHARACTERISTICS:
        ( A ) LENGTH: 375 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

```
Met  Ser  Pro  Leu  Asn  Gln  Ser  Ala  Glu  Gly  Leu  Pro  Gln  Glu  Ala  Ser
1                   5                   10                      15

Asn  Arg  Ser  Leu  Asn  Ala  Thr  Glu  Thr  Ser  Glu  Ala  Trp  Asp  Pro  Arg
               20                  25                      30

Thr  Leu  Gln  Ala  Leu  Lys  Ile  Ser  Leu  Pro  Val  Leu  Leu  Ser  Val  Ile
          35                  40                      45

Thr  Leu  Ala  Thr  Val  Leu  Ser  Asn  Ala  Phe  Val  Leu  Thr  Thr  Ile  Leu
     50                       55                      60

Leu  Thr  Arg  Lys  Leu  His  Thr  Pro  Ala  Asn  Tyr  Leu  Ile  Gly  Ser  Leu
65                       70                  75                            80

Ala  Thr  Thr  Asp  Leu  Leu  Val  Ser  Ile  Leu  Val  Met  Pro  Ile  Ser  Met
               85                       90                      95

Ala  Tyr  Thr  Ile  Thr  His  Thr  Trp  Asn  Phe  Gly  Gln  Ile  Leu  Cys  Asp
               100                 105                      110

Ile  Trp  Leu  Ser  Ser  Asp  Ile  Thr  Cys  Cys  Thr  Ala  Ser  Ile  Leu  His
          115                 120                      125

Leu  Cys  Val  Ile  Ala  Leu  Asp  Arg  Tyr  Trp  Ala  Ile  Thr  Asp  Ala  Leu
     130                 135                      140

Glu  Tyr  Ser  Lys  Arg  Arg  Thr  Ala  Gly  His  Ala  Ala  Thr  Met  Ile  Ala
145                      150                 155                           160

Ile  Val  Trp  Ala  Ile  Ser  Ile  Cys  Ile  Ser  Ile  Pro  Pro  Leu  Phe  Trp
               165                      170                      175

Arg  Gln  Glu  Lys  Ala  Gln  Glu  Glu  Met  Ser  Asp  Cys  Leu  Val  Asn  Thr
               180                      185                      190

Ser  Gln  Ile  Ser  Tyr  Thr  Ile  Tyr  Ser  Thr  Cys  Gly  Ala  Phe  Tyr  Ile
          195                      200                 205

Pro  Ser  Val  Leu  Leu  Ile  Ile  Leu  Tyr  Gly  Arg  Ile  Tyr  Arg  Ala  Ala
     210                      215                 220

Arg  Asn  Arg  Ile  Leu  Asn  Pro  Pro  Ser  Leu  Ser  Gly  Lys  Arg  Phe  Thr
225                      230                 235                           240

Thr  Ala  His  Leu  Ile  Thr  Gly  Ser  Ala  Gly  Ser  Val  Cys  Ser  Leu  Asn
```

|     |     |     |     | 245 |     |     |     | 250 |     |     |     | 255 |     |
|-----|-----|-----|-----|-----|-----|-----|-----|-----|-----|-----|-----|-----|-----|
| Ser | Ser | Leu | His | Glu | Gly | His | Ser | Ser | Ala | Gly | Ser | Pro | Leu Phe |
|     |     |     | 260 |     |     |     | 265 |     |     |     | 270 |     |     |

| Phe | Asn | His | Val | Lys | Ile | Lys | Leu | Ala | Asp | Ser | Ala | Leu | Glu | Arg | Lys |
|     |     | 275 |     |     |     |     | 280 |     |     |     |     | 285 |     |     |     |

| Arg | Ile | Ser | Ala | Ala | Arg | Glu | Arg | Lys | Ala | Thr | Lys | Ile | Leu | Gly | Ile |
|     | 290 |     |     |     |     | 295 |     |     |     |     | 300 |     |     |     |     |

| Ile | Leu | Gly | Ala | Phe | Ile | Ile | Cys | Trp | Leu | Pro | Phe | Phe | Val | Val | Ser |
| 305 |     |     |     |     | 310 |     |     |     |     | 315 |     |     |     |     | 320 |

| Leu | Val | Leu | Pro | Ile | Cys | Arg | Asp | Ser | Cys | Trp | Ile | His | Pro | Gly | Leu |
|     |     |     |     | 325 |     |     |     |     | 330 |     |     |     |     | 335 |     |

| Phe | Asp | Phe | Phe | Thr | Trp | Leu | Gly | Tyr | Leu | Asn | Ser | Leu | Ile | Asn | Pro |
|     |     |     | 340 |     |     |     |     | 345 |     |     |     |     | 350 |     |     |

| Ile | Ile | Tyr | Thr | Val | Phe | Asn | Glu | Glu | Phe | Arg | Gln | Ala | Phe | Gln | Lys |
|     |     | 355 |     |     |     |     | 360 |     |     |     |     | 365 |     |     |     |

| Ile | Val | Pro | Phe | Arg | Lys | Ala |
|     |     | 370 |     |     |     | 375 |

( 2 ) INFORMATION FOR SEQ ID NO:6:

( i ) SEQUENCE CHARACTERISTICS:
        ( A ) LENGTH: 398 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

| Met | Glu | Glu | Pro | Gly | Ala | Gln | Cys | Ala | Pro | Pro | Ala | Pro | Ala | Gly | Ser |
| 1   |     |     |     | 5   |     |     |     |     | 10  |     |     |     |     | 15  |     |

| Glu | Thr | Trp | Val | Pro | Gln | Ala | Asn | Leu | Ser | Ser | Ala | Pro | Ser | Gln | Asn |
|     |     |     | 20  |     |     |     |     | 25  |     |     |     |     | 30  |     |     |

| Cys | Ser | Ala | Lys | Asp | Tyr | Ile | Tyr | Gln | Asp | Ser | Ile | Ser | Leu | Pro | Trp |
|     |     | 35  |     |     |     |     | 40  |     |     |     |     | 45  |     |     |     |

| Lys | Val | Leu | Leu | Val | Met | Leu | Leu | Ala | Leu | Ile | Thr | Leu | Ala | Thr | Thr |
|     | 50  |     |     |     |     | 55  |     |     |     |     | 60  |     |     |     |     |

| Leu | Ser | Asn | Ala | Phe | Val | Ile | Ala | Thr | Val | Tyr | Arg | Thr | Arg | Lys | Leu |
| 65  |     |     |     |     | 70  |     |     |     |     | 75  |     |     |     |     | 80  |

| His | Thr | Pro | Ala | Asn | Tyr | Leu | Ile | Ala | Ser | Leu | Asp | Val | Thr | Asp | Leu |
|     |     |     |     | 85  |     |     |     |     | 90  |     |     |     |     | 95  |     |

| Leu | Val | Ser | Ile | Leu | Val | Ile | Pro | Ile | Ser | Thr | Met | Tyr | Thr | Val | Thr |
|     |     |     | 100 |     |     |     |     | 105 |     |     |     |     | 110 |     |     |

| Asp | Arg | Trp | Thr | Leu | Ser | Gln | Val | Val | Cys | Asp | Phe | Trp | Leu | Ser | Ser |
|     |     | 115 |     |     |     |     | 120 |     |     |     |     | 125 |     |     |     |

| Asp | Ile | Thr | Cys | Cys | Thr | Ala | Ser | Ile | Leu | His | Leu | Cys | Val | Ile | Ala |
|     | 130 |     |     |     |     | 135 |     |     |     |     | 140 |     |     |     |     |

| Leu | Asp | Arg | Tyr | Trp | Ala | Ile | Thr | Asp | Ala | Val | Glu | Tyr | Ser | Ala | Lys |
| 145 |     |     |     |     | 150 |     |     |     |     | 155 |     |     |     |     | 160 |

| Arg | Thr | Pro | Lys | Arg | Ala | Ala | Val | Met | Ile | Ala | Leu | Val | Trp | Val | Phe |
|     |     |     |     | 165 |     |     |     |     | 170 |     |     |     |     | 175 |     |

| Ser | Ile | Ser | Ile | Ser | Leu | Pro | Pro | Phe | Phe | Trp | Arg | Gln | Ala | Lys | Ala |
|     |     |     | 180 |     |     |     |     | 185 |     |     |     |     | 190 |     |     |

```
Glu  Glu  Glu  Val  Ser  Glu  Cys  Val  Val  Asn  Thr  Asp  His  Ile  Leu  Tyr
          195                      200                     205

Thr  Val  Tyr  Ser  Thr  Val  Gly  Ala  Phe  Tyr  Phe  Pro  Thr  Leu  Leu  Leu
          210                      215                     220

Ile  Ala  Leu  Tyr  Gly  Arg  Ile  Tyr  Val  Glu  Ala  Arg  Ser  Arg  Ile  Leu
225                      230                     235                          240

Lys  Gln  Thr  Pro  Asn  Arg  Thr  Gly  Lys  Arg  Leu  Thr  Arg  Ala  Gln  Leu
                    245                      250                          255

Ile  Thr  Asp  Ser  Pro  Gly  Ser  Thr  Ser  Ser  Val  Thr  Ser  Ile  Asn  Ser
                    260                      265                     270

Arg  Val  Pro  Asp  Val  Pro  Ser  Glu  Ser  Gly  Ser  Pro  Val  Tyr  Val  Asn
          275                      280                     285

Gln  Val  Lys  Val  Arg  Val  Ser  Asp  Ala  Leu  Leu  Glu  Lys  Lys  Lys  Leu
          290                      295                     300

Met  Ala  Ala  Arg  Glu  Arg  Lys  Ala  Thr  Lys  Thr  Leu  Gly  Ile  Ile  Leu
305                      310                     315                          320

Gly  Ala  Phe  Ile  Val  Cys  Trp  Leu  Pro  Phe  Phe  Ile  Ile  Ser  Leu  Val
                    325                      330                     335

Met  Pro  Ile  Cys  Lys  Asp  Ala  Cys  Trp  Phe  His  Leu  Ala  Ile  Phe  Asp
                    340                      345                     350

Phe  Phe  Thr  Trp  Leu  Gly  Tyr  Leu  Asn  Ser  Leu  Ile  Asn  Pro  Ile  Ile
               355                      360                     365

Tyr  Thr  Met  Ser  Asn  Glu  Asp  Phe  Lys  Gln  Ala  Phe  His  Lys  Leu  Ile
     370                      375                     380

Arg  Leu  Ser  Ala  Gln  Val  Asp  Leu  Pro  Phe  Ala  Val  Gly  Pro
385                      390                     395
```

( 2 ) INFORMATION FOR SEQ ID NO:7:

( i ) SEQUENCE CHARACTERISTICS:
        ( A ) LENGTH: 471 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

```
Met  Asp  Ile  Leu  Cys  Glu  Glu  Asn  Thr  Ser  Leu  Ser  Ser  Thr  Thr  Asn
1                        5                        10                         15

Ser  Leu  Met  Gln  Leu  Asn  Asp  Asp  Thr  Arg  Leu  Tyr  Ser  Asn  Asp  Phe
               20                      25                      30

Asn  Ser  Gly  Glu  Ala  Asn  Thr  Ser  Asp  Ala  Phe  Asn  Trp  Thr  Val  Asp
          35                      40                      45

Ser  Glu  Asn  Arg  Thr  Asn  Leu  Ser  Cys  Glu  Gly  Cys  Leu  Ser  Pro  Ser
     50                      55                      60

Cys  Leu  Ser  Leu  Leu  His  Leu  Gln  Glu  Lys  Asn  Trp  Ser  Ala  Leu  Leu
65                       70                      75                           80

Thr  Ala  Val  Val  Ile  Ile  Leu  Thr  Ile  Ala  Gly  Asn  Ile  Leu  Val  Ile
                    85                      90                      95

Met  Ala  Val  Ser  Leu  Glu  Lys  Lys  Leu  Gln  Asn  Ala  Thr  Asn  Tyr  Phe
                    100                     105                     110
```

| | | | | | | | | | | | | | |
|---|---|---|---|---|---|---|---|---|---|---|---|---|---|
|Leu|Met|Ser 115|Leu|Ala|Ile|Ala 120|Asp|Met|Leu|Leu|Gly 125|Phe|Leu|Val|Met|
|Pro|Val 130|Ser|Met|Leu|Thr 135|Ile|Leu|Tyr|Gly|Tyr 140|Arg|Trp|Pro|Leu|Pro|
|Ser 145|Lys|Leu|Cys|Ala|Val 150|Trp|Ile|Tyr|Leu|Asp 155|Val|Leu|Phe|Ser|Thr 160|
|Ala|Ser|Ile|Met|His 165|Leu|Cys|Ala|Ile|Ser 170|Leu|Asp|Arg|Tyr|Val 175|Ala|
|Ile|Gln|Asn|Pro 180|Ile|His|His|Ser|Arg 185|Phe|Asn|Ser|Arg|Thr 190|Lys|Ala|
|Phe|Leu|Lys 195|Ile|Ile|Ala|Val|Trp 200|Thr|Ile|Ser|Val|Gly 205|Ile|Ser|Met|
|Pro|Ile 210|Pro|Val|Phe|Gly|Leu 215|Gln|Asp|Asp|Ser|Lys 220|Val|Phe|Lys|Glu|
|Gly 225|Ser|Cys|Leu|Leu|Ala 230|Asp|Asp|Asn|Phe|Val 235|Leu|Ile|Gly|Ser|Phe 240|
|Val|Ser|Phe|Phe|Ile 245|Pro|Leu|Thr|Ile|Met 250|Val|Ile|Thr|Tyr 255|Phe|Leu|
|Thr|Ile|Lys|Ser 260|Leu|Gln|Lys|Glu|Ala 265|Thr|Leu|Cys|Val|Ser 270|Asp|Leu|
|Gly|Thr|Arg 275|Ala|Lys|Leu|Ala|Ser 280|Phe|Ser|Phe|Leu|Pro 285|Gln|Ser|Ser|
|Leu|Ser 290|Ser|Glu|Lys|Leu|Phe 295|Gln|Arg|Ser|Ile|His 300|Arg|Glu|Pro|Gly|
|Ser 305|Tyr|Thr|Gly|Arg 310|Arg|Thr|Met|Gln|Ser 315|Ile|Ser|Asn|Glu|Gln|Lys 320|
|Ala|Cys|Lys|Val|Leu 325|Gly|Ile|Val|Phe|Phe 330|Leu|Phe|Val|Val|Met 335|Trp|
|Cys|Pro|Phe|Phe 340|Ile|Thr|Asn|Ile|Met 345|Ala|Val|Ile|Cys|Lys 350|Glu|Ser|
|Cys|Asn|Glu 355|Asp|Val|Ile|Gly|Ala 360|Leu|Leu|Asn|Val|Phe 365|Val|Trp|Ile|
|Gly|Tyr 370|Leu|Ser|Ser|Ala|Val 375|Asn|Pro|Leu|Val|Tyr 380|Thr|Leu|Phe|Asn|
|Lys 385|Thr|Tyr|Arg|Ser|Ala 390|Phe|Ser|Arg|Tyr|Ile 395|Gln|Cys|Gln|Tyr|Lys 400|
|Glu|Asn|Lys|Lys|Pro 405|Leu|Gln|Leu|Ile|Leu 410|Val|Asn|Thr|Ile|Pro 415|Ala|
|Leu|Ala|Tyr|Lys 420|Ser|Ser|Gln|Leu|Gln 425|Met|Gly|Gln|Lys|Lys 430|Asn|Ser|
|Lys|Gln|Asp 435|Ala|Lys|Thr|Thr|Asp 440|Asn|Asp|Cys|Ser|Met 445|Val|Ala|Leu|
|Gly|Lys 450|Gln|His|Ser|Glu|Glu 455|Ala|Ser|Lys|Asp|Asn 460|Ser|Asp|Gly|Val|
|Asn 465|Glu|Lys|Val|Ser|Cys 470|Val| | | | | | | | | |

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: oligonucleotide ( x i ) SEQUENCE DESCRIPTION: SEQ ID NO:8:

GATGGTACAC TGGCTGGGGG GTGGGCTGAG TTGACGGTGG CT     42

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: oligonucleotide ( x i ) SEQUENCE DESCRIPTION: SEQ ID NO:9:

TACCACGCGG CCAAGAGCCT TTACCA     26

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: oligonucleotide ( x i ) SEQUENCE DESCRIPTION: SEQ ID NO:10:

TGGTGCTAGA GATCTGCTGA CGTTC     25

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: oligonucleotide ( x i ) SEQUENCE DESCRIPTION: SEQ ID NO:11:

GAGAAGTCAG ACACACAGAA AGTCTGTGTA AGTTTTACAA CTTGC     45

-continued ( 2 ) INFORMATION FOR SEQ ID NO:12:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: OLIGONUCLEOTIDE ( x i ) SEQUENCE DESCRIPTION: SEQ ID NO:12:

GATGGTACAC TGGCTGGGGG GTGGGCTGAG TTGACGGTGG CT    4 2

METHODS FOR IDENTIFYING A COMPOUND THAT BINDS TO A HUMAN 5-HT 1E RECEPTOR

This application is a divisional application of U.S. Ser. No. 08/370,542, filed Jan. 9, 1995, now U.S. Pat. No. 5,476,782, issued Dec. 19, 1995, which is a continuation of U.S. Ser. No. 08/194,113, filed Feb. 8, 1994, now abandoned, which is a continuation of U.S. Ser. No. 07/803,626, filed Dec. 2, 1991, now abandoned, the contents of which are hereby incorporated by reference.

BACKGROUND OF THE INVENTION

Since the purification of a pressor substance in blood serum termed serotonin (Rapport et al., 1947) and later identified as 5-hydroxytryptamine (5-HT)(Rapport, 1949), there has been a plethora of reports demonstrating that this indoleamine not only plays a role in the functioning of peripheral tissues but, indeed, performs a key role in the brain as a neurotransmitter. Certainly, the anatomical localization of serotonin and serotonergic neurons in both the peripheral and central nervous systems supports its role in such diverse physiologic and behavioral functions as pain perception, sleep, aggression, sexual activity, hormone secretion, thermoregulation, motor activity, cardiovascular function, food intake and renal regulation (For review see Green, 1985; Osborne and Hamon, 1988; Sanders-Bush, 1988; Peroutka, 1991). Taken together, it appears that serotonin plays an important role in homeostasis and in modulating responsiveness to environmental stimuli. Accordingly, studies demonstrating that abnormalities in the serotonergic system may be associated with disease states has created a drug development effort towards agents which may selectively modulate the function of serotonin (Glennon, 1990).

In relation to the characterization of physiologic or biochemical responses resulting from the release of serotonin are simultaneous investigations examining the receptor sites responsible for the actions elicited by the indoleamine transmitter. Following early in vitro pharmacological assays describing the existence of two different serotonin receptors, designated as D and M, in the guinea pig ileum (Gaddum and Picarelli, 1957), the advent of receptor binding technique in the 1970's has brought to light during the last decade the diversity of 5-HT receptors existing in both the brain and peripheral tissues. Thus, although the concept of D and M receptors has not been invalidated, serotonin receptors not fitting either category have been identified using radioligand methods. To date using this technique, there appears to be four classes of serotonin receptors found in the brain: 5-HT$_1$, 5-HT$_2$, 5-HT$_3$ and, 5-HT$_4$ (Peroutka 1991). Furthermore, 5-HT1 sites have been subclassified as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). Although a detailed characterization of the 5-HT$_{1E}$ binding site is lacking, extensive pharmacologic, biochemical and functional properties have clearly shown that the other four subtypes of 5-HT$_1$ sites are receptors according to classical criteria. Interestingly, the 5-HT$_{1E}$ binding site was first observed in human cortical tissue using [$^3$H]5-HT as the radioligand probe in the presence of 5-carboxyamidotryptamine and mesulergine to mask other members of the 5-HT$_1$ receptor class. The affinity constants of the nine drugs tested indicated a unique pharmacological profile. In particular, the low affinity of 5-CT and ergotamine seemed to clearly discriminate the pharmacologically defined 5-HT$_{1D}$ site from that of this novel serotonergic site. Importantly, it was demonstrated that 5-HT$_{1E}$ sites are saturable and exist in a density consistent with other known neurotransmitter receptors. Furthermore, this site appeared to interact with a GTP-binding protein. Overall, the data provided a framework suggesting that the 5-HT$_{1E}$ binding site may represent a functional receptor.

During the last few years, the field of molecular biology has provided an important facet to receptor research by cloning these proteins and allowing more precise characterizations in isolated systems (Hartig et al., 1990). This has been accomplished for the 5-HT$_{1A}$ (Fargin et al., 1988), 5-HT$_{1C}$ (Julius et al., 1988), 5-HT$_{1D}$ (Branchek et al., 1990) and 5-HT$_2$ receptors (Pritchett et al., 1988). Thus, there is no doubt that these binding sites represent "true" functional receptors. Indeed, the pharmacological characterization of serotonin receptors involved in various physiological or biochemical functions is a key component of drug development for the serotonergic system. As one can deduce from the diversity of serotonin binding sites, many targets are available for advancement in selective drug design. The coupling of molecular biological methods to pharmacological characterization particularly for cloned human receptors will open new avenues for pharmaceutical development which have not been previously explored.

SUMMARY OF THE INVENTION

This invention provides an isolated nucleic acid molecule encoding a human 5-HT$_{1E}$ receptor.

This invention also provides an isolated protein which is a human 5-HT$_{1E}$ receptor.

This invention provides a vector comprising an isolated nucleic acid molecule encoding a human 5-HT$_{1E}$ receptor.

This invention also provides vectors such as plasmids comprising a DNA molecule encoding a human 5-HT$_{1E}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding the 5-HT$_{1E}$ receptor as to permit expression thereof.

This invention provides a mammalian cell comprising a DNA molecule encoding a human 5-HT$_{1E}$ receptor.

This invention provides a method for determining whether a ligand not known to be capable of binding to a human 5-HT$_{1E}$ receptor can bind to a human 5-HT$_{1E}$ receptor which comprises contacting a mammalian cell comprising an isolated DNA molecule encoding a human 5-HT$_{1E}$ receptor with the ligand under conditions permitting binding of ligands known to bind to a 5-HT$_{1E}$ receptor, detecting the presence of any of the ligand bound to a human 5-HT$_{1E}$ receptor, and thereby determining whether the ligand binds to a human 5-HT$_{1E}$ receptor.

This invention also provides a method for determining whether a ligand not known to be capable of binding to the human 5-HT$_{1E}$ receptor can functionally activate its activity or prevent the action of a ligand which does so. This comprises contacting a mammalian cell comprising an isolated DNA molecule which encodes a human 5-HT$_{1E}$ receptor with the ligand under conditions permitting the activation or blockade of a functional response, detected by means of a bioassay from the mammalian cell such as a second messenger response, and thereby determining whether the ligand activates or prevents the activation of the human 5-HT$_{1E}$ receptor functional output.

This invention further provides a method of screening drugs to identify drugs which specifically interact with, and bind to, the human 5-HT$_{1E}$ receptor on the surface of a cell which comprises contacting a mammalian cell comprising an isolated DNA molecule encoding a human 5-HT$_{1E}$ receptor with a plurality of drugs, determining those drugs which bind to the mammalian cell, and thereby identifying drugs which specifically interact with, and bind to, a human 5-HT$_{1E}$ receptor.

This invention also provides a method of screening drugs to identify drugs which interact with, and activate or block the activation of, the human 5-HT$_{1E}$ receptor on the surface of a cell which comprises contacting the mammalian cell comprising an isolated DNA molecule encoding and expressing a human 5-HT$_{1E}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1E}$ receptor.

This invention provides a nucleic acid probe comprising nucleic acid molecule of at least 15 nucleotides capable of specifically hybridizing with a sequence included within the sequence of a nucleic acid molecule encoding a human 5-HT$_{1E}$ receptor.

This invention also provides a method of detecting expression of the 5-H$_{1E}$ receptor on the surface of a cell by detecting the presence of mRNA coding for a 5-HT$_{1E}$ receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1E}$ receptor under hybridizing conditions, detecting the presence of mRNA hybridized to the probe, and thereby detecting the expression of the 5-HT$_{1E}$ receptor by the cell.

This invention provides an antisense oligonucleotide having a sequence capable of binding specifically with any sequences of an mRNA molecule which encodes a human 5-HT$_{1E}$ receptor so as to prevent translation of the mRNA molecule.

This invention provides an antibody directed to a human 5-HT$_{1E}$ receptor.

This invention provides a transgenic nonhuman mammal expressing DNA encoding a human 5-HT$_{1E}$ receptor. This invention also provides a transgenic nonhuman mammal expressing DNA encoding a human 5-HT$_{1E}$ receptor so mutated as to be incapable of normal receptor activity, and not expressing native 5-HT$_{1E}$ receptor. This invention further provides a transgenic nonhuman mammal whose genome comprises antisense DNA complementary to DNA encoding a human 5-HT$_{1E}$ receptor so placed as to be transcribed into antisense mRNA which is complementary to mRNA encoding a 5-HT$_{1E}$ receptor and which hybridizes to mRNA encoding a 5-HT$_{1E}$ receptor thereby reducing its translation.

This invention provides a method of determining the physiological effects of expressing varying levels of human 5-HT$_{1E}$ receptors which comprises producing a transgenic nonhuman animal whose levels of human 5-HT$_{1E}$ receptor expression are varied by use of an inducible promoter which regulates human 5-HT$_{1E}$ receptor expression.

This invention also provides a method of determining the physiological effects of expressing varying levels of human 5-HT$_{1E}$ receptors which comprises producing a panel of transgenic nonhuman animals each expressing a different amount of human 5-HT$_{1E}$ receptor.

This invention provides a method for diagnosing a predisposition to a disorder associated with the expression of a specific human 5-HT$_{1E}$ receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human 5-HT$_{1E}$ receptor and labelled with a detectable marker; e. detecting labelled bands which have hybridized to the DNA encoding a human 5-HT$_{1E}$ receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated 5-HT$_{1E}$ receptor which comprises inducing cells to express 5-HT$_{1E}$ receptor, recovering the receptor from the resulting cells and purifying the receptor so recovered.

This invention also provides a method of preparing the isolated 5-HT$_{1E}$ receptor which comprises inserting nucleic acid encoding 5-HT$_{1E}$ receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention also provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides a transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

BRIEF DESCRIPTION OF THE FIGURES

FIG. 1. Nucleotide and deduced amino acid sequence of gene 5-HT$_{1E}$. (Seq. I.D. Nos. 1 and 2).

Numbers above the nucleotide sequence indicate nucleotide position. DNA sequence was determined by the chain termination method of Sanger, et al., on denatured double-stranded plasmid templates using the enzyme Sequenase. Deduced amino acid sequence (single letter code) of a long open reading frame is shown.

FIG. 2. Comparison of the human 5-HT$_{1E}$ receptor primary structures with other serotonin receptors. (Seq. I.D. Nos. 3-5HT$_{1A}$; 4-5HT$_{1C}$; 5-5HT$_{1D\alpha}$; 6-5HT$_{1D\beta}$; 7-5HT$_2$)

Amino acid sequences (single letter code) are aligned to optimize homology. The putative transmembrane spanning domains are indicated by stars and identified by Roman numerals (TM I-VII).

Figure 3:
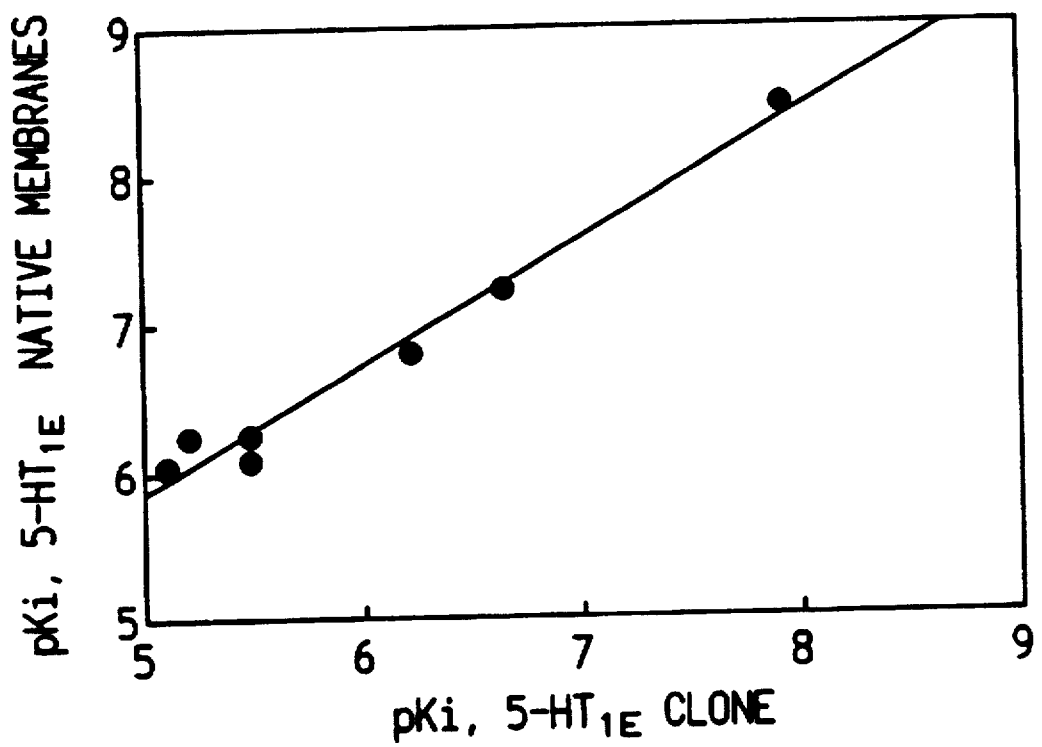

FIG. 3. Respective pKi values of various drugs for the inhibition of [$^3$H]5-HT specific binding to the cloned 5-HT$_{1E}$ receptor and human cortical membrane preparations containing the native 5-HT$_{1E}$ receptor.

Values for the native membrane preparation are taken from Leonhardt et al., 1989. "r" is the correlation coefficient between pKi values calculated for the two receptor preparations and clearly indicates the similarity in binding profile.

Figure 4:
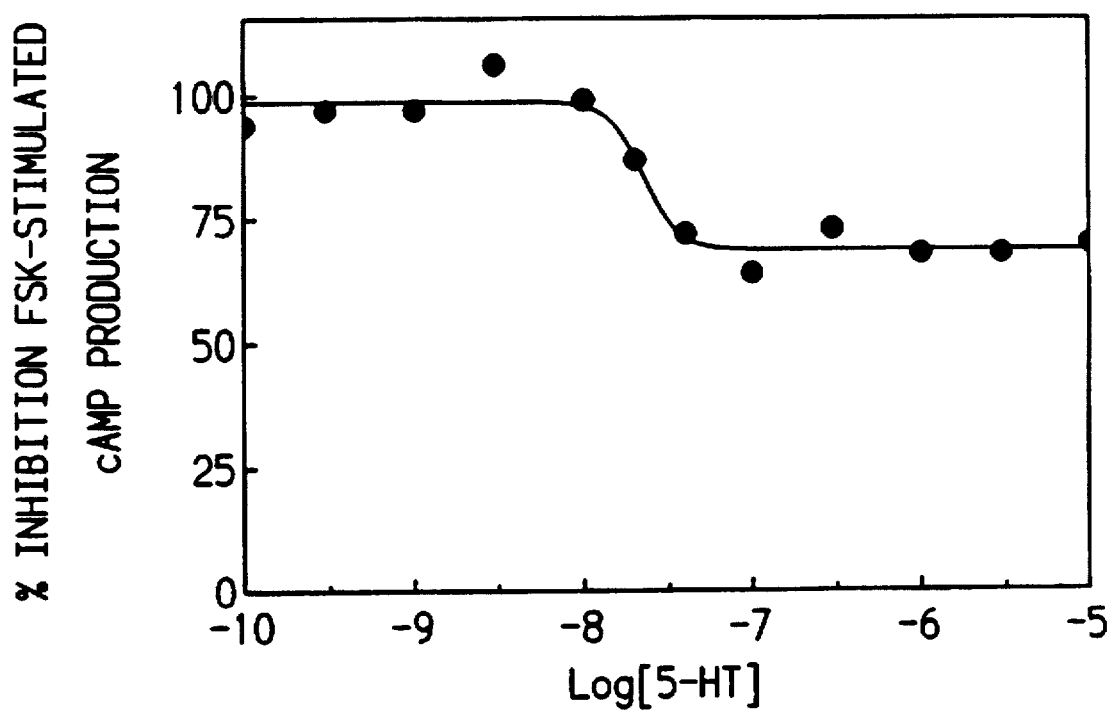

FIG. 4. 5-HT concentration-effect curve for the inhibition of forskolin-stimulated cAMP formation in Y1 cells transfected with the 5HT$_{1E}$ receptor.

Values are expressed as a percentage of forskolin(Fsk) stimulated cAMP production.

FIG. 5. 5HT$_{1E}$ mRNA localization in the human brain.

cDNA was reverse transcribed from total RNA (5 μg) using random hexamers (500 pmoles). One microgram of cDNA was subjected to 30 cycles of PCR amplification using 5'- and 3'-primers directed to the third cytoplasmic loop of the 5HT1E receptor gene. Amplified fragments were subjected to Southern blot analysis using an end-labeled oligonucleotide probe which was internal to the PCR primers. (+) control consisted of 5HT1E recombinant plasmid; (−) control consisted of all cDNA and PCR reagents without the addition of cDNA template. Intensity of signal is depicted as the number of plus signs as defined in the figure key.

DETAILED DESCRIPTION OF THE INVENTION

As used herein, the 5-HT receptor family is defined as the group of mammalian proteins that function as receptors for serotonin. A 5-HT receptor subfamily is defined as a subset of proteins belonging to the 5-HT receptor family which are encoded by genes which exhibit homology of greater than 72% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Four human 5-HT receptor subfamilies can be distinguished based on the information presently available: 5-HT$_1$, 5-HT$_2$, 5-HT$_3$ and 5-HT$_4$ (Peroutka, 1991). The 5-HT$_2$ receptor subfamily contains the human 5-HT$_2$ receptor. Although no other human members of this family have been described, the rat 5-HT$_2$ receptor (Pritchett, et al. 1988; Julius, et al. Proc. Natl. Acad. Sci. USA 87:928–932, 1990) and the rat 5HT$_{1C}$ receptor (Julius, et al. 1988) constitute a rat 5-HT receptor subfamily. The 5-HT$_1$ subfamily has been subdivided further as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). The 5-HT$_{1A}$ subfamily contains the human 5-HT$_{1A}$ receptor, also known as G-21 (Fargin, et al. 1988) The 5-HT$_{1D}$ receptor subfamily contains two members, the 5-HT$_{1D-1}$ receptor (also termed 5-HT$_{1D\alpha}$) and the 5-HT$_{1D-2}$ receptor (also termed 5-HT$_{1D\beta}$). The 5-HT$_{1E}$ subfamily contains the human 5-HT$_{1E}$ receptor (also termed clone. hp75d). Although this definition differs from the pharmacological definition used earlier, there is significant overlap between the present definition and the pharmacological definition. Members of the 5-HT$_{1E}$ receptor subfamily so described include the 5-HT$_{1E}$ receptor and any other receptors which have a greater than 72% homology to the DNA and amino acid sequence shown in FIG. 1 according to the definition of "subfamily". This invention relates to the discovery of the first member of the human 5-HT$_{1E}$ receptor subfamily.

This invention provides an isolated nucleic acid molecule encoding a human 5HT$_{1E}$ receptor. As used herein, the term "isolated nucleic acid molecule" means a nucleic acid molecule that is, a molecule in a form which does not occur in nature. Such a receptor is by definition a member of the 5-HT$_{1E}$ receptor subfamily. Therefore, any receptor which meets the defining criteria given above is a human 5-HT$_{1E}$ receptor. One means of isolating a human 5-HT$_{1E}$ receptor is to probe a human genomic library with a natural or artificially designed DNA probe, using methods well known in the art. DNA probes derived from the human receptor gene 5-HT$_{1E}$ are particularly useful probes for this purpose. DNA and cDNA molecules which encode human 5-HT$_{1E}$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human 5-HT$_{1E}$ receptor. Such molecules may have coding sequences substantially the same as the coding sequence shown in FIG. 1. The DNA molecule of FIG. 1 encodes the sequence of the human 5-HT$_{1E}$ receptor gene.

This invention further provides a cDNA molecule of encoding a human 5-HT$_{1E}$ receptor having a coding sequence substantially the same as the coding sequence shown in FIG. 1. This molecule is obtained by the means described above.

This invention also provides an isolated protein which is a human 5-HT$_{1E}$ receptor. As used herein, the term "isolated protein" means a protein molecule free of other cellular components. An example of such protein is an isolated protein having substantially the same amino acid sequence as the amino acid sequence shown in FIG. 1 which is a human 5-HT$_{1E}$ receptor. One means for obtaining isolated 5-HT$_{1E}$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human 5-HT$_{1E}$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIG. 1 and designated clone hp75d (Seq. I.D. No. 1).

This invention also provides vectors comprising a DNA molecule encoding a human 5-$HT_{1E}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human 5-$HT_{1E}$ receptor as to permit expression thereof. DNA having coding sequences substantially the same as the coding sequence shown in FIG. 1 may usefully be inserted into the vectors to express human 5-$HT_{1E}$ receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human 5-$HT_{1E}$ receptor and the regulatory elements necessary for expression of the DNA in the bacterial, yeast, or mammalian cell so located relative to the DNA encoding a human 1-$HT_{1E}$ receptor as to permit expression thereof. Some plasmids adapted for expression in a mammalian cell are pSVL (available from Pharmacia, Piscataway, N.J.) and pcEXV-3 (Miller J. and Germain R. N., J. Exp. Med. 164:1478 (1986)). A specific example of such plasmid is a plasmid adapted for expression in a mammalian cell comprising cDNA having coding sequences substantially the same as the coding sequence shown in FIG. 1 and the regulatory elements necessary for expression of the DNA in the mammalian cell which is designated pcEXV-hp75d and deposited under ATCC Accession No. 75138. Those skilled in the art will readily appreciate that numerous plasmids adapted for expression in a mammalian cell which comprise DNA of encoding human 5-$HT_{1E}$ receptors and the regulatory elements necessary to express such DNA in the mammalian cell may be constructed utilizing existing plasmids and adapted as appropriate to contain the regulatory elements necessary to express the DNA in the mammalian cell.

The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human 5-$HT_{1E}$ receptor, such as a mammalian cell comprising a plasmid adapted for expression in a mammalian cell, which comprises a DNA molecule encoding a human 5-$HT_{1E}$ receptor, the protein encoded thereby is expressed on the cell surface, and the regulatory elements necessary for expression of the DNA in the mammalian cell so located relative to the DNA encoding a human 5-$HT_{1E}$ receptor as to permit expression thereof. Numerous mammalian cells may be used as hosts, including, for example, the mouse fibroblast cell NIH3T3, CHO cells, HeLa cells, Ltk⁻ cells, Y1 cells, etc. A particular example of an Ltk⁻ cell is a cell designated 5-$HT_{1E}$-7 and deposited under ATCC Accession No. CRL 10913 and comprises the plasmid designated pcEXV-hp75d. Another example is the murine adrenal Y1 cell line designated Y-5-$HT_{1E}$ and deposited under ATCC Accession No. CRL 10914. Expression plasmids such as that described supra may be used to transfect mammalian cells by methods well known in the art such as calcium phosphate precipitation, or DNA encoding these 5-$HT_{1E}$ receptors may be otherwise introduced into mammalian cells, e.g., by microinjection, to obtain mammalian cells which comprise DNA, e.g., cDNA or a plasmid, encoding either human 5-$HT_{1E}$ receptor.

This invention provides a method for determining whether a ligand not known to be capable of binding to a human 5-$HT_{1E}$ receptor can bind to a human 5-$HT_{1E}$ receptor which comprises contacting a mammalian cell comprising a DNA molecule encoding a human 5-$HT_{1E}$ receptor, the protein encoded thereby is expressed on the cell surface, with the ligand under conditions permitting binding of ligands known to bind to the ⁵-$HT_{1E}$ receptor, detecting the presence of any of the ligand bound to the 5-$HT_{1E}$ receptor, and thereby determining whether the ligand binds to the 5-$HT_{1E}$ receptor. This invention also provides a method for determining whether a ligand not known to be capable of binding to the human 5-$HT_{1E}$ receptor can functionally activate its activity or prevent the action of a ligand which does so. This comprises contacting a mammalian cell comprising an isolated DNA molecule which encodes a human 5-$HT_{1E}$ receptor with the ligand under conditions permitting the activation or blockade of a functional response, detected by means of a bioassay from the mammalian cell such as a second messenger response, and thereby determining whether the ligand activates or prevents the activation of the human 5-$HT_{1E}$ receptor functional output. The DNA in the cell may have a coding sequence substantially the same as the coding sequence shown in FIG. 1 preferably, the mammalian cell is nonneuronal in origin. An example of a nonneuronal mammalian cell is an Ltk⁻ cell, in particular the Ltk⁻ cell designated 5-$HT_{1E}$-7. Another example of a nonneuronal mammalian cell to be used for functional assays is a Y1 murine adrenal cell, specifically the Y1 cell designated Y-5-$HT_{1E}$. The preferred method for determining whether a ligand is capable of binding to the human 5-$HT_{1E}$ receptor comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{1E}$ receptor on its surface, or contacting a membrane preparation derived from such a transfected cell, with the ligand under conditions which are known to prevail, and thus to be associated with, in vivo binding of the ligands to a 5-HT$_{1E}$ receptor, detecting the presence of any of the ligand being tested bound to the 5-HT$_{1E}$ receptor on the surface of the cell, and thereby determining whether the ligand binds to, activates or prevents the activation of the 5-HT$_{1E}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{1E}$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{1E}$ receptor. The transfection system is also useful for determining the affinity and efficacy of known drugs at the human 5-HT$_{1E}$ receptor sites.

This invention also provides a method of screening drugs to identify drugs which specifically interact with, and bind to, the human 5-HT$_{1E}$ receptor on the surface of a cell which comprises contacting a mammalian cell comprising a DNA molecule encoding a human 5-HT$_{1E}$ receptor on the surface of a cell with a plurality of drugs, determining those drugs which bind to the mammalian cell, and thereby identifying drugs which specifically interact with, and bind to, the human 5-HT$_{1E}$ receptor. This invention also provides a method of screening drugs to identify drugs which interact with, and activate or block the activation of, the human 5-HT$_{1E}$ receptor or the surface of a cell which comprises contacting the mammalian cell comprising an isolated DNA molecule encoding and expressing a human 5-HT$_{1E}$ receptor with a plurality of drugs, determining those drugs which activate or block the activation of the receptor in the mammalian cell using a bioassay such as a second messenger assays, and thereby identifying drugs which specifically interact with , and activate or block the activation of, a human 5-HT$_{1E}$ receptor. The DNA in the cell may have a coding sequence substantially the same as the coding sequence shown in FIG. 1. Preferably, the mammalian cell is nonneuronal in origin. An example of a nonneuronal mammalian cell is an Ltk$^-$ cell, in particular the Ltk$^-$ cell designated 5-HT$_{1E}$-7. Another example of a non-neuronal mammalian cell to be used for functional assays is a Y1 murine adrenal cell, specifically the Y1 cell designated Y-5-HT$_E$. Drug candidates are identified by choosing chemical compounds which bind with high affinity to the expressed 5-HT$_{1E}$ receptor protein in transfected cells, using radioligand binding methods well known in the art, examples of which are shown in the binding assays described herein. Drug candidates are also screened for selectivity by identifying compounds which bind with high affinity to one particular 5-HT$_{1E}$ receptor subtype but do not bind with high affinity to any other serotonin receptor subtype or to any other known receptor site. Because selective, high affinity compounds interact primarily with the target 5-HT$_{1E}$ receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human 5-HT$_{1E}$ receptor, for example with a coding sequence included within the sequence shown in FIG. 1. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human 5-HT$_{1E}$ receptors is useful as a diagnostic test for any disease process in which levels of expression of the corresponding 5-HT$_{1E}$ receptor is altered. DNA probe molecules are produced by insertion of a DNA molecule which encodes human 5-HT$_{1E}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human 5-HT$_{1E}$ receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the 5-HT$_{1E}$ gene by in situ hybridization. An example of such an oligonucleotide is: GATGGTACACTGGCTGGGGGGTGGGCTGAGTTGACGGTGGCT (Seq. I.D. No. 8).

This invention also provides a method of detecting expression of a 5-HT$_{1E}$ receptor on the surface of a cell by detecting the presence of mRNA coding for a 5-HT$_{1E}$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1E}$ receptor under hybridizing conditions, detecting the presence of mRNA hybridized to the probe, and thereby detecting the expression of the 5-HT$_{1E}$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting.

However, other methods for performing these steps are well known to those skilled in the art, and the discussion above is merely an example.

This invention provides an antisense oligonucleotide having a sequence capable of binding specifically with any sequences of an mRNA molecule which encodes a human 5-HT$_{1E}$ receptor so as to prevent translation of the mRNA molecule. The antisense oligonucleotide may have a sequence capable of binding specifically with any sequences of the cDNA molecule whose sequence is shown in FIG. 1. As used herein, the phrase "binding specifically" means the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human 5-HT$_{1E}$ receptor by passing through a cell membrane and binding specifically with mRNA encoding a human 5-HT$_{1E}$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIG. 1 may be used as the oligonucleotides of the pharmaceutical composition.

This invention also provides a method of treating abnormalities which are alleviated by reduction of expression of a 5-HT$_{1E}$ receptor which comprises administering to a subject an amount of the pharmaceutical composition described above effective to reduce expression of the 5-HT$_{1E}$ receptor by the subject. This invention further provides a method of treating an abnormal condition related to 5-HT$_{1E}$ receptor activity which comprises administering to a subject an amount of the pharmaceutical composition described above effective to reduce expression of the 5-HT$_{1E}$ receptor by the subject. Several examples of such abnormal conditions are dementia, Parkinson's disease, feeding disorders, pathological anxiety, schizophrenia, or a migraine headache.

Antisense oligonucleotide drugs inhibit translation of mRNA encoding these receptors. Synthetic oligonucleotides, or other antisense chemical structures are designed to bind to mRNA encoding the 5-HT$_{1E}$ receptor and inhibit translation of mRNA and are useful as drugs to inhibit expression of 5-HT$_{1E}$ receptor genes in patients. This invention provides a means to therapeutically alter levels of expression of human 5-HT$_{1E}$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIG. 1 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of $5\text{-HT}_{1E}$ receptors.

This invention provides an antibody directed to the human $5\text{-HT}_{1E}$ receptor, for example a monoclonal antibody directed tb an epitope of a human $5\text{-HT}_{1E}$ receptor present on the surface of a cell and having an amino acid sequence substantially the same as an amino acid sequence for a cell surface epitope of the human $5\text{-HT}_{1E}$ receptor included in the amino acid sequence shown in FIG. 1 (Seq. I.D. No. 2). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 1 will bind to a surface epitope of a human $5\text{-HT}_{1E}$ receptor, as described. Antibodies directed to human $5\text{-HT}_{1E}$ receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequence shown in FIG. 1 (Seq. I.D. No. 2). As a still further alternative, DNA, such as a cDNA or a fragment thereof, may be cloned and expressed and the resulting polypeptide recovered and used as an immunogen. These antibodies are useful to detect the presence of human $5\text{-HT}_{1E}$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human $5\text{-HT}_{1E}$ receptor effective to block binding of naturally occurring ligands to the $5\text{-HT}_{1E}$ receptor, and a pharmaceutically acceptable carrier. A monoclonal antibody directed to an epitope of a human $5\text{-HT}_{1E}$ receptor present on the surface of a cell and having an amino acid sequence substantially the same as an amino acid sequence for a cell surface epitope of the human $5\text{-HT}_{1E}$ receptor included in the amino acid sequence shown in FIG. 1 is useful for this purpose.

This invention also provides a method of treating abnormalities which are alleviated by reduction of expression of a human $5\text{-HT}_{1E}$ receptor which comprises administering to a subject an amount of the pharmaceutical composition described above effective to block binding of naturally occurring ligands to the $5\text{-HT}_{1E}$ receptor and thereby alleviate abnormalities resulting from overexpression of a human $5\text{-HT}_{1E}$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of $5\text{-HT}_{1E}$ receptor activity which comprises administering to a subject an amount of the pharmaceutical composition described above effective to block binding of naturally occurring ligands to the $5\text{-HT}_{1E}$ receptor and thereby alleviate the abnormal condition. Some examples of abnormal conditions are dementia, Parkinson's disease, feeding disorders, pathological anxiety, schizophrenia, and a migraine headache.

This invention provides a method of detecting the presence of a $5\text{-HT}_{1E}$ receptor on the surface of a cell which comprises contacting the cell with an antibody directed to the human $5\text{-HT}_{1E}$ receptor, under conditions permitting binding of the antibody to the receptor, detecting the presence of the antibody bound to the cell, and thereby the presence of the human $5\text{-HT}_{1E}$ receptor on the surface of the cell. Such a method is useful for determining whether a given cell is defective in expression of $5\text{-HT}_{1E}$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human $5\text{-HT}_{1E}$ receptor. This invention also provides a transgenic nonhuman mammal expressing DNA encoding a human $5\text{-HT}_{1E}$ receptor so mutated as to be incapable of normal receptor activity, and not expressing native $5\text{-HT}_{1E}$ receptor. This invention also provides a transgenic nonhuman mammal whose genome comprises antisense DNA complementary to DNA encoding a human $5\text{-HT}_{1E}$ receptor so placed as to be transcribed into antisense mRNA which is complementary to mRNA encoding a $5\text{-HT}_{1E}$ receptor and which hybridizes to mRNA encoding a $5\text{-HT}_{1E}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIG. 1. An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of human $5\text{-HT}_{1E}$ receptors are produced by creating transgenic animals in which the expression of a $5\text{-HT}_{1E}$ receptor is either increased or decreased, or the amino acid sequence of the expressed $5\text{-HT}_{1E}$ receptor protein is altered, by a variety of techniques. Examples of these techniques include: 1) Insertion of normal or mutant versions of DNA encoding a human $5\text{-HT}_{1E}$ receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these $5\text{-HT}_{1E}$ receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human $5\text{-}HT_{1E}$ receptor is purified from a vector (such as plasmid pCEXV-hp75d described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these $5\text{-}HT_{1E}$ receptors even before such drugs become available. These animal model systems are useful for predicting or evaluating possible therapeutic applications of drugs which activate or inhibit these $5\text{-}HT_{1E}$ receptors by inducing or inhibiting expression of the native or trans-gene and thus increasing or decreasing expression of normal or mutant $5\text{-}HT_{1E}$ receptors in the living animal. Thus, a model system is produced in which the biological activity of drugs directed against these $5\text{-}HT_{1E}$ receptors are evaluated before such drugs become available. The transgenic animals which over or under produce the $5\text{-}HT_{1E}$ receptor indicate by their physiological state whether over or under production of the $5\text{-}HT_{1E}$ receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which downregulates or acts as an antagonist to $5\text{-}HT_{1E}$ receptor is indicated as worth developing, and if a promising therapeutic application is uncovered by these animal model systems, activation or inhibition of the $5\text{-}HT_{1E}$ receptor is achieved therapeutically either by producing agonist or antagonist drugs directed against these $5\text{-}HT_{1E}$ receptors or by any method which increases or decreases the expression of these $5\text{-}HT_{1E}$ receptors in man.

This invention provides a method of determining the physiological effects of expressing varying levels of human $5\text{-}HT_{1E}$ receptors which comprises producing a transgenic nonhuman animal whose levels of human $5\text{-}HT_{1E}$ receptor expression are varied by use of an inducible promoter which regulates human $5\text{-}HT_{1E}$ receptor expression. This invention also provides a method of determining the physiological effects of expressing varying levels of human $5\text{-}HT_{1E}$ receptors which comprises producing a panel of transgenic nonhuman animals each expressing a different amount of human $5\text{-}HT_{1E}$ receptor. Such animals may be produced by introducing different amounts of DNA encoding a human $5\text{-}HT_{1E}$ receptor into the oocytes from which the transgenic animals are developed.

This invention also provides a method for identifying a substance capable of alleviating abnormalities resulting from overexpression of a human $5\text{-}HT_{1E}$ receptor comprising administering the substance to a transgenic nonhuman mammal expressing at least one artificially introduced DNA molecule encoding a human $5\text{-}HT_{1E}$ receptor and determining whether the substance alleviates the physical and behavioral abnormalities displayed by the transgenic nonhuman mammal as a result of overexpression of a human $5\text{-}HT_{1E}$ receptor. As used herein, the term "substance" means a compound or composition which may be natural, synthetic, or a product derived from screening. Examples of DNA molecules are DNA or cDNA molecules having a coding sequence substantially the same as the coding sequence shown in FIG. 1.

This invention provides a pharmaceutical composition comprising an amount of the substance described supra effective to alleviate the abnormalities resulting from overexpression of $5\text{-}HT_{1E}$ receptor and a pharmaceutically acceptable carrier.

This invention further provides a method for treating the abnormalities resulting from overexpression of a human $5\text{-}HT_{1E}$ receptor which comprises administering to a subject an amount of the pharmaceutical composition described above effective to alleviate the abnormalities resulting from overexpression of a human $5\text{-}HT_{1E}$ receptor.

This invention provides a method for identifying a substance capable of alleviating the abnormalities resulting from underexpression of a human $5\text{-}HT_{1E}$ receptor comprising administering the substance to the transgenic nonhuman mammal described above which expresses only nonfunctional human $5\text{-}HT_{1E}$ receptor and determining whether the substance alleviates the physical and behavioral abnormalities displayed by the transgenic nonhuman mammal as a result of underexpression of a human $5\text{-}HT_{1E}$ receptor.

This invention also provides a pharmaceutical composition comprising an amount of a substance effective to alleviate abnormalities resulting from underexpression of $5\text{-}HT_{1E}$ receptor and a pharmaceutically acceptable carrier.

This invention further provides a method for treating the abnormalities resulting from underexpression of a human $5\text{-}HT_{1E}$ receptor which comprises administering to a subject an amount of the pharmaceutical composition described above effective to alleviate the abnormalities resulting from underexpression of a human $5\text{-}HT_{1E}$ receptor.

This invention provides a method for diagnosing a predisposition to a disorder associated with the expression of a specific human $5\text{-}HT_{1E}$ receptor allele which comprises: a)

obtaining DNA of subjects suffering from the disorder; b) performing a restriction digest of the DNA with a panel of restriction enzymes; c.electrophoretically separating the resulting DNA fragments on a sizing gel; d) contacting the resulting gel with a nucleic acid probe capable of specifically hybridizing to DNA encoding a human 5-$HT_{1E}$ receptor and labelled with a detectable marker; e) detecting labelled bands which have hybridized to the DNA encoding a human 5-$HT_{1E}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-$HT_{1E}$ receptor allele.

This invention provides a method of preparing the isolated 5-$HT_{1E}$ receptor which comprises inducing cells to express 5-$HT_{1E}$ receptor, recovering the receptor from the resulting cells, and purifying the receptor so recovered. An example of an isolated 5-$HT_{1E}$ receptor is an isolated protein having substantially the same amino acid sequence as the amino acid sequence shown in FIG. 1. For example, cells can be induced to express receptors by exposure to substances such as hormones. The cells can then be homogenized and the receptor isolated from the homogenate using an affinity column comprising, for example, serotonin or another substance which is known to bind to the receptor. The resulting fractions can then be purified by contacting them with an ion exchange column, and determining which fraction contains receptor activity or binds anti-receptor antibodies.

This invention provides a method of preparing the isolated 5-$HT_{1E}$ receptor which comprises inserting nucleic acid encoding 5-$HT_{1E}$ receptor in a suitable vector, inserting the resulting vector in a suitable host cell, recovering the receptor produced by the resulting cell, and purifying the receptor so recovered. An example of an isolated 5-$HT_{1E}$ receptor is an isolated protein having substantially the same amino acid sequence as the amino 35 acid sequence shown in FIG. 1. This method for preparing 5-$HT_{1E}$ receptor uses recombinant DNA technology methods well known in the art. For example, isolated nucleic acid encoding 5-$HT_{1E}$ receptor is inserted in a suitable vector, such as an expression vector. A suitable host cell, such as a bacterial cell, or a eukaryotic cell such as a yeast cell, is transfected with the vector. 5-$HT_{1E}$ receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

Applicants have identified individual receptor subtype proteins and have described methods for the identification of pharmacological compounds for therapeutic treatments. Pharmacological compounds which are directed against specific receptor subtypes provide effective new therapies with minimal side effects.

This invention identifies for the first time a new receptor protein, its amino acid sequence, and its human gene. Furthermore, this invention describes a previously unrecognized group of receptors within the definition of a 5-$HT_{1E}$ receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human cDNA and genomic clone encoding a 5-$HT_{1E}$ receptor. A new human gene for the receptor identified herein as 5-$HT_1$ has been identified and characterized, and a series of related cDNA and genomic clones have been isolated. In addition, the human 5-$HT_{1E}$ receptor has been expressed in Ltk⁻ cells and Y1 cells by transfecting the cells with the plasmid pcEXV-hp75d. The pharmacological binding properties of the protein encoded have been determined, and these binding properties classify this protein as a serotonin 5-$HT_{1E}$ receptor. Mammalian cell lines expressing this human 5-$HT_{1E}$ receptor at the cell surface have been constructed, thus establishing the first well-defined, cultured cell lines with which to study this 5-$HT_{1E}$ receptor.

The invention will be better understood by reference to the Experimental Details which follow, but those skilled in the art will readily appreciate that the specific experiments detailed are only illustrative of the invention as described more fully in the claims which follow thereafter.

MATERIALS and METHODS
Cloning and Sequencing

A human placental genomic library (Stratagene) was screened using oligonucleotides derived from the human 5-$HT_{1D\beta}$ receptor gene (U.S. Ser. No. 520,716), as a probe. Overlapping oligomers complementary to the 5-$HT_{1D\beta}$ sequence in transmembrane domains III, V and VI were labeled with $^{32}$p-dATP and $^{32}$p-dCTP by synthesis with the large fragment of DNA Polymerase (Maniatis et al., 1982). Hybridization was performed at 40° C. in a solution containing 25% formamide, 10% dextran sulfate, 5×SSC (1×SSC is 0.15M sodium chloride, 0.015M sodium citrate), 1×Denhardt's (0.02% polyvinylpyrrolidone, 0.02% Ficoll, and 0.02% bovine serum albumin), and 200 µg/ml of sonicated salmon sperm DNA. The filters were washed at 40° C. in 0.1×SSC containing 0.1% sodium dodecyl sulfate (SDS) and exposed at −70° C. to Kodak XAR film in the presence of an intensifying screen. Lambda phage hybridizing to the probe were plaque purified and DNA was prepared for Southern blot analysis (Southern, 1975; Maniatis et al., 1982). For subcloning and further Southern blot analysis DNA was inserted into pUC18 (Pharmacia, Piscataway, N.J.). Nucleotide sequence analysis was done by the Sanger dideoxy nucleotide chain-termination method (Sanger 1977) on denatured double-stranded plasmid templates using Sequenase (U.S. Biochemical Corp., Cleveland, Ohio.).

Expression

The entire coding region of clone hp75d was cloned into the eukaryotic expression vector pcEXV-3 (Miller, 1986). Stable cell lines were obtained by cotransfection with the plasmid pcEXV-3 (containing the 5-HT$_{1E}$ receptor gene) and the plasmid pGCcos3neo (containing the aminoglycoside transferase gene) into Ltk$^-$ cells and Y1 cells using calcium phosphate (reagents obtained from Specialty Media, Lavellette, N.J.). The cells were grown in a controlled environment (37° C., 5% $CO_2$) as monolayers in Dulbecco's modified Eagle medium (Gibco, Grand Island, N.Y.) or Flo Medium Specialty Media, Inc., Lavallette, N.J.) containing 25 mM glucose and supplemented with 10% bovine calf serum, 100 U/ml penicillin G and 100 µg/ml streptomycin sulfate. Stable clones were then selected for resistance to the antibiotic G-418 and harvested membranes were screened for their ability to bind [$^3$H]serotonin.

Detection of 5-HT$_{1E}$ Receptor mRNA in Brain Using PCR

Total RNA from human brain tissue was extracted using the RNasol protocol as described by the manufacturer. cDNA was prepared from 5 µg of total RNA with random hexanucleotide primers (500 pmoles) using Superscript reverse transcriptase (BRL, MD.) in 50 mM Tris-HCL pH8.3 buffer containing 40u RNasin, 2.5 mM $MgCl_2$, 50 mM KCL and 1 mM dNTPs, at 42° C. for 1 hr. The reaction was stopped by heating at 95° C. for 5 min. and chilled on ice. After terminating the reaction, RNase H (2u) was added and incubated at 37° C. for 20 min. An aliquot (1 µg) of the first strand cDNA A was diluted (1:5) into a 50 µl PCR reaction mixture (200 µM dNTPs final concentration) containing 1.25 U of Taq polymerase (Cetus Corp., Calif.) in the buffer supplied by the manufacturer, and 1 µM of 5' primer= 5' ACCACGCGGCCAAGAGCCTTTACCA 3' (Seq. I.D. No. 9) and 3' primer= 5'TGGTGCTAGAGATCTGCTGACGTTC 3' (Seq. I.D. No. 10), oligonucleotides derived from the third cytoplasmic loop region. The PCR amplification reaction was carried out on a Perkin Elmer Cetus thermal cycler by first a 5 min. incubation at 95° C. followed by 30 rounds of the following cycle: 2 min. at 94° C., 2 min. at 42° C., 3 min. at 72° C., with a 3" extension, followed at the end by a 15 min. incubation at 72° C. In order to control for the amplification of DNA (carried over during the RNA extraction), control PCR reactions were run in parallel with RNA diluted in the same manner as the cDNA samples. If necessary, RNA samples were pretreated with RNase-free DNase to eliminate any contaminating DNA. Positive controls were included in all experiments, consisting of plasmid containing 5HT12E receptor gene sequences. The products of the PCR amplification were separated by electrophoresis in 1.5% agarose. Amplified fragments were identified by blotting the gel to nitrocellulose and probing with an oligonucleotide internal to the 5'- and 3'-primers (5'-GAGAAGTCAGACACACAGAAAGTCTGTGTAAGTT-TTACAACTTGC 3') (Seq. I.D. No. 11) and end-labeled with [c-$^{32}$P]ATP using $T_4$ polynucleotide kinase. Hybridization was performed at 40° C. in a solution containing 50% formamide, 10% dextran sulfate, 5×SSC (1×SSC is 0.15M sodium chloride, 0.015M sodium citrate), 1×Denhardt's (0.02% polyvinylpyrrolidone, 0.02% Ficoll, and 0.02% bovine serum albumin), and 200 µg/ml of sonicated salmon sperm DNA. The filters were washed at 50° C. in 0.1×SSC containing 0.1% sodium dodecyl sulfate and exposed at −70° C. to Kodak XAR film in the presence of an intensifying screen.

Membrane Preparation

Membranes were prepared from transfected Ltk$^-$ cells which were grown to 100% confluency. The cells were washed twice with phosphate-buffered saline, scraped from the culture dishes into 5 ml of ice-cold phosphate-buffered saline, and centrifuged at 200×g for 5 min at 4° C. The pellet was resuspended in 2.5 ml of ice-cold Tris buffer (20 mM Tris -HCl, pH 7.4 at 23° C., 5 mM EDTA) and homogenized by a Wheaton tissue grinder. The lysate was subsequently centrifuged at 200×g for 5 min at 4° C. to pellet large fragments which were discarded. The supernatant was collected and centrifuged at 40,000×g for 20 min at 4° C. The pellet resulting from this centrifugation was washed once in ice-cold Tris buffer and finally resuspended in a final buffer containing 50 mM Tris-HCl and 0.5 mM EDTA, pH 7.4 at 23 C. Membrane preparations were kept on ice and utilized within two hours for the radioligand binding assays. Protein concentrations were determined by the method of Bradford (1976) using bovine serum albumin as the standard.

Radioligand Binding

[$^3$H]5HT binding was performed using slight modifications of the 5-HT$_{1E}$ assay conditions reported by Leonhardt et al. (1989) with the omission of masking ligands. Radioligand binding studies were achieved at 37° C. in a total volume of 250 µl of buffer (50 mM Tris, 10 mM $MgCl_2$, 0.2 mM EDTA, 10 µM pargyline, 0.1 % ascorbate, pH 7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 min for both saturation and displacement studies based upon initial investigations which determined equilibrium binding conditions. Nonspecific binding was defined in the presence of 10 µM 5-HT. Binding was initiated by the addition of 50 µl membrane homogenates (10–20 µg). The reaction was terminated by rapid filtration through presoaked (0.5% polyethyleneimine) filters using 48R Cell Brandel Harvester (Gaithersburg, Md.). Subsequently, filters were washed for 5 seconds with ice cold buffer (50 mM Tris HCL, pH 7.4 at 40° C.), dried and placed into vials containing 2.5 ml of Readi-Safe (Beckman, Fullerton, Calif.) and radioactivity was measured using a Beckman LS 5000TA liquid scintillation counter. The efficiency of counting of [$^3$H]5HT averaged between 45–50%. Binding data was analyzed by computer-assisted nonlinear regression analysis (Accufit and Accucomp, Lundon Software, Chagrin Falls, Ohio.). IC$_{50}$ values were converted to Ki values using the Cheng-Prusoff equation (1973). All experiments were performed in triplicate.

Measurement of cAMP Formation

Transfected Y1 cells (expression level=688 fmol/ mg of protein) were incubated in DMEM, 5 mM theophylline, 10 mM Hepes (4-[2-Hydroxyethyl]-1-piperazineethanesulfonic acid), 10 µM pargyline, for 20 minutes at 37° C., 5% $CO_2$. A 5-HT dose-effect curve was then conducted by adding 12 different final concentrations of drug ranging from 10 uM to 0.1 nM, followed immediately by the addition of forskolin (10 µM). Subsequently, the cells were incubated for an additional 10 minutes at 37° C., 5% $CO_2$. The media was aspirated and the reaction terminated by the addition of 100 mM HCl. The plates were stored at 4° C. for 15 minutes and centrifuged for 5 minutes (500×g at 4° C.) to pellet cellular debris. Aliquots of the supernatant fraction were then stored at −20° C. prior to assessment of cAMP formation by radioimmunoassay (cAMP Radioimmunoassay kit, Advanced Magnetics, Cambridge, Mass.).

DETECTION OF 5-$HT_{1E}$ RECEPTOR mRNA IN BRAIN USING IN SITU HYBRIDIZATION HISTOCHEMISTRY

Labeling of 5-$HT_{1E}$ receptor oligo probe with digoxigenin-11-dUTP

The 5-$HT_{1E}$ receptor oligo probe (45 mer sequence: GATGGTACACTGGCTGGGGGGTGGGCTGAGTTGA-CGGTGGCT) (Seq. I.D. No. 12) was synthesized in Molecular Biology Department of Neurogenetic Corp. The 3' end tailing reaction was as follows: To a sterile 1.5 ml Eppendorf tube add (1) 8 µl of 5-$HT_{1E}$ receptor oligo probe (520 ng, denatured at 95° C., then chilled on ice); (2) 8 µl of 5×tailing buffer (BRL); (3) 5 µl of digoxigenin-11-dUTP (Boehringer); (4) 4 µl of dATP at 1/50 dilution; (5) 7 µl of terminal transferase (TdT, BRL); (6) 7 µl of distilled water. The above reaction mixture was incubated at 37° C. for 5 min. The tailed oligo probe was purified by ethanol precipitation, vacuum dried and reconstituted in 40 µl of distilled water.

Tissue Preparation

Guinea pig brains were dissected and frozen, first in methylbutane, then on dry ice. Brain sections were cut at 11 µm on a cryostat, thaw-mounted on gelatin-coated slides, and stored at −80° C. On the day of the experiment, the brain sections were quickly brought to room temperature using a cool air stream, and fixed in 3% paraformaldehyde made up in 0.1M PBS containing 0.02% diethylpyrocarbonate (DEPC). After rinsed in 0.1M PBS and 2×SSC, the tissue sections were dehydrated in graded ethanol and air dried.

Prehybridization

All the tissue sections were pre-incubated with hybridization buffer in a humid chamber at 25° C. for 1 hr. Twenty ml of the hybridization buffer contained (1). 10 ml of 100% formamide; (2) 4 ml of 20×SSC; (3) 0.4 ml of 50×Denhardts; (4) 1.0 ml of 10 mg/ml salmon sperm DNA; (5) 0.5 ml of 10 mg/ml yeast tRNA: (6) 4 ml of Dextran sulfate.

Hybridization

The digoxigenin labeled 5-$HT_{1E}$ oligo probe (40 µl) was diluted in 1 ml of hybridization buffer. Each tissue section was then covered with 0.1 ml of the hybridization buffer with probe and incubated at 40° C. for 82 hr. After incubation all the sections were washed in 2×SSC (25° C., 1 hr), in 1×SSC (25° C., 1 hr), finally in 0.5×SSC, first 37° C. 30 min, then 25° C. 30 min.

Immunological Detection

Following the post-hybridization washes slides were rinsed in Buffer #1 (100 mM Tris-HCl; 150 mM NaCl; pH 7.5) for 1 min, then incubated with 2% normal sheep serum plus 0.3% triton X-100 in Buffer #1 for 30 min. After this preparation the sections were incubated with anti-digoxigenin conjugated with alkaline phosphatase at dilution 1:500 in Buffer #1 containing 1% normal sheep serum and 0.3% triton X-100 at RT for 1.5 hr, then at 4° C. overnight. The next day the tissue sections were rinsed in Buffer #1 for 10 min, then in Buffer #2 (100 mM Tris-HCl; 100 mM NaCl; 50 mM $MgCl_2$; pH9.5) for 10 min. The chromogen solution was prepared immediately before the colorimetric reaction: i.e. to 10 ml of Buffer #2, (1) 45 µl of 4-nitro blue tetrazolium chloride (NBT, 75 mg/ml in 70% dimethylformamide); (2) 35 µl of 5-bromo-4-chloro-3-indolyl-phosphate (x-phosphate, 50 mg/ml in 100% dimethylformamide); and (3) 2.5 mg of levamisole were added. In order to carry out the colorimetric reaction sections were incubated with the chromogen solution in a humid, light-tight box overnight. The chromogen reaction was halted by rinsing the slides in Buffer #3 (10 mM Tris-HCl; 1 mM EDTA; pH 8.0). The sections were then rinsed in PBS, covered with Aquamount, and examined under a light microscope.

Drugs

[$^3$H]5-HT (specific activity=28 Ci/mmole) was obtained from New England Nuclear, Boston, Mass. All other chemicals were obtained from commercial sources and were of the highest grade purity available.

RESULTS

Isolation of a Genomic Clone Encoding a 5$HT_{1E}$ Receptor

A human genomic placental library was screened with oligonucleotide probes derived from transmembrane domains III, V and VI of the 5-$HT_{1D\beta}$ receptor gene. The hybridization of these probes with the library was performed at low stringency and the result was the appearance of several hundred positive signals. Subsequently, approximately 350 of these clones were purified and categorized into various groups, based upon which of the three probes were responsible for the hybridization signal associated with a given clone. One group of clones exhibited hybridization signals with both transmembrane domain probes III and V. A number of these clones were subject to Southern blot analysis and determined to be identical or overlapping clones. A representative of this group, hp75d, was further characterized by nucleic acid sequence analysis and encoded what appeared to be a new serotonin receptor based upon its deduced amino acid sequence.

Nucleotide Sequence and Deduced Amino Acid Sequence of hp75d

DNA sequence information obtained from clone hp75d is shown in FIG. 1. An open reading frame extending from an ATG start codon at position 1 to a stop codon at position 1095 can encode a protein 365 amino acids in length, having a relative molecular mass ($M_r$) of 41,633. A comparison of this protein sequence with previously characterized neurotransmitter receptors indicates that hp75d encodes a receptor which is a new member of a family of molecules which span the lipid bilayer seven times and couple to guanine nucleotide regulatory proteins (the G protein-coupled receptor family). A variety of structural features which are invariant in this family were present including the aspartic acid residues of transmembrane regions II and III, the DRY sequence at the end of transmembrane region III, and the conserved proline residues of transmembrane regions IV, V, VI and VII (Hartig et al. and references therein), were present in clone hp75d. A comparison of the transmembrane homology of hp75d to the other cloned serotonin receptors is shown in FIG. 2 and exhibits the following order of identity: $5\text{-HT}_{1D\alpha}$ (65%), $5\text{-HT}_{1D\beta}$ (64%), $5\text{-HT}_{1A}$ (52%), $5\text{-HT}_{1C}$ (40%) and $5\text{-HT}_2$ (39%).

Receptor Expression in Transfected Mammalian Cells

Saturation analysis of membranes prepared from stably transfected Ltk⁻ cells demonstrated that the receptor expressed was saturable and of high affinity. Scatchard plot analysis by non-linear regression revealed a Kd of 10.3±1.2 nM (mean±S.E.M., n=7) and a Bmax consistent with a high level of expression, 10.9±2.6 picomoles/mg of protein (mean±S.E.M., n=7). The percent specific binding determined at the measured Kd value for [³H]5-HT was greater than 85% of total binding. Furthermore, evidence that the receptor is coupled to a G-protein was demonstrated by the ability of Gpp(NH)p, a non-hydrolyzable analog of GTP, to inhibit the specific binding of [³H]5-HT (IC$_{50}$=1885±556, n$_H$=0.87±0.04, I$_{max}$=26.4±5.6%).

Pharmacological analysis of the receptor was accomplished by testing the ability of drugs from different chemical classes to displace [³H]5-HT specific binding (Table 1). Of the compounds investigated, 5-HT and 5-hydroxylated tryptamine derivatives possessed the highest affinity which according to the classification system of Peroutka

TABLE 1

Ki (nM) values of various drugs for the inhibition of [³H]5-HT specific binding to clonal 5-HT$_{1E}$ cell membranes. Binding assays were performed with 4.5–5.5 nM of [³H]5-HT and 10–12 different concentrations of each inhibitory drug. Ki values were calculated from the IC$_{50}$ values using the Cheng-Prusoff equation. Each value is the mean ± S.E.M. of 3–4 independent determinations.

| COMPOUND | Ki (nM) |
|---|---|
| 5-NT | 10.9 ± 1.0 |
| Lyserpol | 42.8 ± 5.3 |
| Ergonavine | 87.7 ± 7.6 |
| Methylergonavine | 89.4 ± 4.2 |
| a-Methyl-5-NT | 121 ± 13 |
| Methiothepin | 194 ± 4 |
| 1-Napthylpiperazine | 207 ± 69 |
| Methysergide | 228 ± 16 |
| Oxymetazoline | 419 ± 49 |
| 5-Methoxy-N,N-DMT | 528 ± 32 |
| Ergotamine | 599 ± 39 |
| 2-Methyl-5-NT | 817 ± 203 |
| Yohimbine | 1270 ± 233 |
| Sumatriptan | 2520 ± 135 |
| Tryptamine | 2559 ± 827 |
| DCl | 2970 ± 592 |
| 5-Methoxytryptamine | 3151 ± 1041 |
| 8-OH-OPAT | 3333 ± 310 |
| Rauaolacine | 3434 ± 102 |
| Spiperone | 5051 ± 689 |
| TFNPP | 6293 ± 259 |
| 5-CT | 7875 ± 284 |
| Ketanserin | >10,000 |
| Pindolol | >10,000 |
| Zacopride | >10,000 |
| LY-165163 (PAPP) | >10,000 |
| DP-5-CT | >10,000 | and Snyder (1979) makes this site a member of the 5-HT$_1$ class. Interestingly, 5-CT possessed low affinity and, thus, discriminates this receptor from that of the 5-HT$_{1D}$ receptor as well as other members of this class. Various ergoline compounds also bound with high affinity including agents which have potent hallucinogenic activity. Excluding methiothepin and 1-napthylpiperazine (Ki values=194 and 207 nM, respectively), piperazine derivatives had low affinity and displayed Ki values greater than 700 nM. Furthermore, rauwolfia alkaloids and serotonergic agents that possess high affinity for various subtypes of receptor within the serotonin family including ketanserin (5-HT$_2$), 8-OH-DPAT (5-HT$_{1A}$), DOI (5-HT$_{1C}$/5-HT$_2$), spiperone (5-HT$_{1A}$/5-HT$_2$), pindolol (5-HT$_{1A}$/5-HT$_{1B}$) and zacopride (5-HT$_3$) had very poor affinity. In all cases, the Hill Coefficients did not differ significantly from unity. Taken together, the pharmacological profile of the 5-HT$_{1E}$ receptor is unique and contrasts to that of other known serotonin receptors. Accordingly, the probability of developing selective drugs for this receptor subtype is increased. Additional supporting evidence that the 5-HT$_{1E}$ receptor is functionally coupled to a G-protein was obtained by testing the ability of 5-HT to inhibit forskolin-stimulated cAMP production in Y1 cells transfected with the 5-HT$_{1E}$ receptor. FIG. 4 demonstrates that the endogenous indoleamine, 5-HT, produced a concentration-related decrease in forskolin-stimulated cAMP production with an EC$_{50}$ of 23.1 nM. The maximum inhibition of cAMP production was 32%.

The tissue distribution of 5HT$_{1E}$ receptor mRNA was detected using PCR technology on cDNA from tissue-derived total RNA. The mRNA localization in human brain tissues demonstrates the presence of 5HT$_{1E}$ in: frontal cortex, cerebellar cortex, temporal cortex, choroid plexus, hippocampus, brain stem and cortex. We have not identified an area of the brain which does not contain 5HT$_{1E}$. We conclude that the 5HT$_{1E}$ mRNA is abundant in human brain. These findings suggest that the 5HT$_{1E}$ receptor is not restricted to any one region of the brain and possibly cell type, but is expressed in numerous neuronal cell groups in many distinct regions of the human brain, as has been described for ⁵HT$_{1C}$.

The presence of 5HT$_{1E}$ receptor mRNA in various regions of the human brain suggest that 5HT$_{1E}$ may modulate a number of the central actions attributed to serotonin. The abundance of 5HT$_{1E}$ receptors (mRNA) in the hippocampus may affect mood, behavior and hallucinogenesis. A greater understanding of possible physiological roles of this receptor subtype may be realized by the development of more specific 5HT$_{1E}$ receptor drugs as well as physiological manipulations of 5HT$_{1E}$ mRNAs/receptors.

The cellular localization of 5-HT$_{1E}$ receptor mRNA was detected with digoxigenin-11-dUTP labeled oligo probes employing in situ hybridization(ISHH) technology. Digoxigenin-11-dUTP labeled oxytocin(OT) oligo probes were used as a positive control for the experiment since the distribution of OT neurons in the central nervous system is well known. OT cells were intensely stained in the Guinea Pig's hypothalamus. Tissue sections pre-treated with RNase A were used as a negative control. Guinea pig brain sections were examined under a light microscope. 5-HT$_{1E}$ receptor mRNA was found in cells located in the frontal cortex, piriform cortex, hippocampus (CA1, CA2 and CA3), lateral septal nucleus, triangular septal nucleus, septofimbrial nucleus and the basal ganglia (caudate-putamen and globus pallidus). It was detected in the amygdaloid complex, the bed nucleus stria terminalis and the hypothalamic area including anterior hypothalamus, periventricular nucleus, paraventricular nucleus (magnocellular and parvocellular populations), supraoptic nucleus which seemed to include both vasopressin and oxytocin cell populations, and the lateral hypothalamus. The 1E receptor mRNA was also detected in the thalamic area including anteroventral thalamic, anterodorsal thalamic, mediodorsal thalamic, ventrolateral thalamic, reticular thalamic paracentral thalamic, paratenial thalamic nuclei and the nucleus stria medullaris. Control sections pre-treated with RNase A did not exhibit any staining pattern.

Experimental Discussion

The deduced amino acid sequence of hp75d was analyzed to uncover relationships between it and the other cloned serotonin receptor sequences. Although the homology within the membrane spanning domains was greatest with the 5-HT$_{1D\alpha}$ receptor (FIG. 2), the nature of this newly cloned receptor could not be clearly predicted. The rational for this ambiguity is the interpretation of the transmembrane domain homology (approximately 65%) to the 5-HT$_{1D\alpha}$ and 5-HT$_{1D\beta}$ receptor subfamily. Closely related members of a "subfamily" of serotonin receptors (i.e. "subtypes") generally share a common transmitter and also have similar pharmacological profiles and physiological roles (for example, 5-HT$_2$ and 5-HT$_{1C}$ or 5-HT$_{1D\alpha}$ and 5-HT$_{1D\beta}$). Such "subtypes" display an amino acid identity of approximately 75–80% in their transmembrane domains. Serotonin receptors which are not members of the same "subfamily", but are members of the serotonin "family" (in which the receptors use the same neurotransmitter; i.e. 5-HT$_2$ and 5-HT$_{1D\alpha}$) generally show much lower transmembrane homology (approximately 45%). Such transmembrane amino acid homologies can, therefore, give insight into the relationship between receptors and be used as predictors of receptor pharmacology. According to this type of analysis, although the newly cloned receptor appears to be more related to the 5-HT$_{1D}$ subfamily, it is likely to be in a subfamily distinct from all the other serotonin receptors.

The present pharmacological evidence substantiates the existence of a novel serotonin receptor in the human brain as first suggested by Leonhardt et al. (1989). Comparison of the pharmacological profile observed in native cortical membranes to that revealed for the cloned 5-HT$_{1E}$ receptor yielded a correlation coefficient of 0.987 (FIG. 3). Indeed, there were some differences in measured affinity constants but the relative values of selected drugs performed in both studies was similar. In this regard, a close examination of the Scatchard plot analysis performed in the study by Leonhardt et al. (1989) reveals that the reported Kd value may have been underestimated since the radioligand concentrations did not exceed 10 nM. In order to have accurately determined the dissociation constant, the radioligand concentration should have been extended to at least 50 nM or 10 times the estimated Kd (Yamamura et al., 1985). The initial study, however, was limited in tissue supply and lacked a comprehensive pharmacological characterization. The cloning of the 5-HT$_{1E}$ site will now allow more extensive investigations into the nature of this unique receptor.

The structure-activity relationships observed in the present study suggest that there are important requirements for high affinity binding to the 5-HT$_{1E}$ receptor. Substitution or removal of the 5-hydroxy group on serotonin decreases the affinity 300 fold for the receptor (egs., tryptamine, 5-methoxytryptamine and 5-carboxyamidotryptamine). Additionally, 2-methylation and α-methylation of 5-HT essentially abolishes its affinity for the 5-HT$_{1E}$ site. In contrast to these substitutions, N,N -dimethylation of the aliphatic side chain of the indole ring increases the affinity approximately 20 fold (unpublished observations). Basic structural requirements of the ergoline derivatives demonstrate that N-methylation of the indole ring decreases affinity as does bulky substitutions. Furthermore, piperazine derivatives are not bound at high affinity.

Notably, the application of the human 5-HT$_{1E}$ receptor clone to pharmaceutical research can lead to new drug design and development. The localization of this receptor in the cerebral cortex (Leonhardt et al., 1989) and parts of the basal ganglia such as the putamen and globus pallidus (Lowther et al., 1991) suggests a putative link to limbic, cognitive and/or motor function (Nieuwenhuys et al., 1988; Kandel and Schwartz, 1985) and, thus, may be involved in such abnormal conditions as dementia, Parkinson's disease, feeding disorders, anxiety and schizophrenia. Notably, the ergot compounds that possess affinity for this site have been demonstrated to affect these type of behaviors in humans as well as animals (Wilkinson and Dourish, 1991). In relation to this, it appears that the 5-HT$_{1E}$ binding site is also present in rat and bovine brain (Leonhardt et al., 1989) as well as guinea-pig, rabbit and dog where the data was initially interpreted as evidence for subtypes of the 5-HT$_{1D}$ receptor (Middlemiss, 1990). Nonetheless, it must be taken into consideration that this novel site can possibly lead to selective drug therapy devoid of side effects. In regard to this, serotonin uptake blockers are effective in treating neuropsychiatric disorders such as depression and obsessive-compulsive illness (Blier et al., 1987; Asberg et al., 1986; Insel et al., 1985). However, these agents have side effects and, in fact, the mechanism of action for these compounds are not linked to any particular serotonergic receptor. The possibility that agents selective for the 5-HT$_{1E}$ receptor may have clinical utility as antidepressants, for example, without the side effects attributed to current treatment modalities can have significant implications for drug therapy. Furthermore, it should be noted that ergoline derivatives have had clinical usefulness as drugs capable of relieving migraines and, thus, the involvement of the 5-HT$_{1E}$ receptor in this disorder deserves future attention. Ultimately, in depth investigations into the localization of the 5-HT$_{1E}$ receptor in brain and peripheral tissue will target new sites that can lead to specific functional roles for this serotonergic receptor.

Another consideration for therapeutic application of this site may be related to the treatment of feeding disorders such as obesity, bulimia nervosa and/or anorexia nervosa. The involvement of serotonin and feeding behavior has received much attention during the last decade. It is now known that many of the identified and well-characterized serotonergic receptors are capable of modulating feeding (Blundell and Lawton, 1990). Notably, serotonin uptake blockers which have been used to treat feeding disorders act nonselectively and as such have side-effect potential (Jimerson et al., 1990). Although many different serotonergic receptors are involved in feeding, the search for the one site that can be exploited for selective drug development has yet to be found. There is no doubt that interest exists in finding drugs that interact with the serotonin system for the treatment of feeding disorders (Cooper, 1989). Thus, the pharmacological profile of the cloned human 5-HT$_{1E}$ receptor is unique and contrasts to other known serotonergic receptors. The utility of this site expressed in a cellular system and, thus, isolated for study will create excellent opportunities in drug development directed towards a novel serotonergic receptor that may have wide-range implications for drug therapy. Indeed, the potential therapeutic applications may extend to neuropsychiatric disorders including depression, anxiety, schizophrenia, dementia and obsessive-compulsive illness as well as obesity and migraine. The localization of 5-HT$_{1E}$ receptor mRNA by in situ hybridization makes it possible to predict its physiological and pathological functions. 5-HT$_{1E}$ receptor mRNA is detected in the limbic structures, such as the hippocampus, septal nuclei, piriform cortex (olfactory system), amygdaloid complex and the bed nucleus stria terminalis. The olfactory system sends afferent fibers to the hippocampus through the subiculum, and to the amygdaloid complex (Kupfermann,1985). In turn the outputs of the hippocampus project to the septal area and hypothalamus while the amygdaloid complex projects to the hypothalamus via the stria terminalis (Kupfermann, 1985). The involvement of the limbic system in emotional behavior (e.g., fear, pleasure,sexual activities) and memory is well known (Kupfermann,1985). Therefore, the finding of 5-HT$_{1E}$ receptor mRNA in these structures indicates a potential role in neuropsychiatric disorders such as depression, obsessive-compulsive illness, anxiety, schizophrenia and dementia.

The hypothalamus regulates the body adjustments to the external and internal environments. It can control hunger (the ventromedial nucleus and the lateral hypothalamus), endocrine functions (e.g. the supraoptic nucleus, the paraventricular nucleus and the periventricular nucleus), affective (emotional) behavior (the ventromedial and dorsomedial nuclei) and the activity of the visceral nervous system (the anterior hypothalamus) (Diamond et al., 1985). The discovery of 5-HT$_{1E}$ receptor mRNA in these nuclei indicates physiological and pathological roles of this receptor subtype in cardiovascular, gastrointestinal, endocrine, neurological and psychiatric systems.

The thalamus is a relay station where the sensory and motor-related pathways passing up the brain stem synapse before proceeding on to the cerebral cortex for more elaborate integration and analysis. The 5-HT$_{1E}$ receptor mRNA was found in the anterior thalamic nucleus which receives the input from the mammillothalamic tract and sends fibers to the cingulate gyrus. Thus, this nucleus is an important part of the circuit connecting the hypothalamus, the thalamus, and the limbic lobe (Diamond et al., 1985). The 5-HT$_{1E}$ receptor mRNA was also found in the mediodorsal thalamic nucleus which is involved in emotional behavior and in the ventral lateral thalamic nucleus which connects the basal ganglia and premotor area. Furthermore, 5-HT$_{1E}$ receptor mRNA was found in the nucleus reticularis thalami through which pass most of the thalamocortical and corticothalamic fibers. The axons of corticothalamic and thalamocortical neurons provide collaterals for synapse with reticular cells, exerting a facilitatory effect, while the axons of the GABA-rich reticularis cells project back on the specific thalamic neurons, continuously modulating (by inhibition) the ascending flow of thalamocortical impulses (Diamond et al., 1985). The reticularis neurons play a significant role in the interactions between the thalamus and the frontal cortex. In addition, the 5-HT$_{1E}$ receptor mRNA was also visualized in the basal ganglia including the caudate-putamen and globus pallidus both of which control motor activity (Alheid et al., 1990). These findings indicate important roles of the 5-HT$_{1E}$ receptors in emotional behavior, sensation (e.g., pain) and motor activity.

REFERENCES

Alheid, G. F.; Heimer, L. & Switzer III, R. C., In: The Human Nervous System. Ed. George Paxinos, Academic Press, Inc., 1990.

Asberg, M., Eriksson, B., Matensson, B., Traskman-Bendz, L. and Wagner, A.: Therapeutic effects of serotonin uptake inhibitors in depression. J. Clin. Psychiat. 47:23–35, 1986.

Blier, P., DeMontigny, C. and Chaput, Y.: Modifications of the serotonin system by antidepressant treatments: Implications for the therapeutic response in major depression. J. Clin. Psychpharmacol. 7(6):24s–35s, 1987.

Blundell, J. E. and Lawton, C. L.: Serotonin receptor subtypes and the organization of feeding behaviour: Experimental models. In: Serotonin: From cell biology to pharmacology and therapeutics. (eds. Paoletti, R., Vanhoutte, P. M., Brunello, N. and Maggi, F. M.) Boston:Kluwer Academic Publishers, pp. 213–219, 1990.

Bradford, M.: A rapid and sensitive method for the quantification of microgram quantities of protein utilizing the principle of protein-dye binding. Anal. Biochem. 72:248–254, 1976.

Branchek, T., Weinshank, R. L., Macchi, M. J., Zgombick, J. M. and Hartig, P. R.: Cloning and expression of a human 5-HT1D receptor. The Second IUPHAR Satellite Meeting on Serotonin, Basel, Switzerland, Jul. 11–13, 1990, Abstract # 2.

Cheng, Y. C. and Prusoff, W. H.: Relationship between the inhibition constant (Ki) and the concentration of inhibitor which causes 50% inhibition (IC50) of an enzyme reaction. Biochem. Pharmacol. 22:3099–3108, 1973.

Cooper, S. J.: Drugs interacting with 5-HT systems show promise for treatment of eating disorders. TIPS 10:56–57, 1989.

Diamond, M. C.; Scheibel, A. B. and Elson, L. M.: The human brain coloring book. Barnes & Noble Books, 1985

Fargin, A., Raymond, J. R., Lohse, M. J., Kobilka, B. K. Caron, M. G. and Lefkowitz, R. J.: The genomic clone G-21 which resembles a B-adrenergic receptor sequence encodes the 5-HT1A receptor. Nature 335:358–360, 1988.

Gaddum, J. H. and Picarelli, Z. P.: Two kinds of tryptamine receptor. Brit. J. Pharmacol. 12:323–328, 1957.

Glennon, R. A.: Serotonin receptors: Clinical implications. Neurosci. Biobehav. Rev. 14:35–47, 1990.

Green, A. R.: Neuropharmacology of serotonin. Oxford: Oxford University Press, 1985.

Hamon, M., Lanfumey, L., El Mestikawy, S., Boni, C., Miquel, M. -C., Bolanos, F., Schechter, L. and Gozlan, H.: The main features of central 5-HT1 receptors. Neuropsychopharmacol. 3(5/6):349–360, 1990.

Hartig, P. R., Kao, H. -T., Macchi, M., Adham, N., Zgombick, J., Weinshank, R. and Branchek, T.: The molecular biology of serotonin receptors: An overview. Neuropsychopharmacol. 3(5/6):335–347, 1990.

Insel, T. R., Mueller, E. A., Alterman, I., Linnoila, M. and Murphy, D. L.: Obsessive-compulsive disorder and serotonin: Is there a connection? Biol. Psychiat. 20:1174–1188, 1985.

Jimerson, D. C., Lesem, M. D., Hegg, A. P. and Brewerton, T. D.: Serotonin in human eating disorders. Ann. N.Y. Acad. Sci. 600:532–544, 1990.

Julius, D., MacDermott, A. B., Axel, R. and Jessell, T. M.: Molecular characterization of a functional cDNA encoding the serotonin 1C receptor. Science 241:558–564, 1988.

Kandel, E. R. and Schwartz, J. H.: Principles of neuroscience. New York: Elsevier Publishing Co., 1985.

Kupfermann, I.: Hypothalamus and limbic system. In: Principles of neuroscience. Eds: Kandel, E. R. and Schwartz, J. H., New York: Elsevier Publishing Co., 1985

Leonhardt, S., Herrick-Davis, K. and Titeler, M.: Detection of a novel serotonin receptor subtype (5-HT1E) in human brain: Interaction with a GTP-binding protein. J. Neurochem. 53(2):465–471, 1989.

Lowther, S., De Paermentier, F., Crompton, M. R., Katona, C. L. E. and Horton, R. W.: 5HT$_{1D}$ and 5HT$_{1E}$ binding sites in depression: A postmortem study in suicide victims. Serotonin 1991—5-Hydroxytryptamine—CNS Receptors and Brain Function, Birmingham, UK, Jul. 14–17, 1991, p. 175, Abstract # P. 145.

Maniatis, T., Fritsch, E. F., and Sambrook, J. Molecular Cloning: A Laboratory Manual, Cold Spring Harbor Laboratory, Cold Spring Harbor, N.Y., 1982.

Middlemiss, D. N., Suman-Chauhan, N., Smith, S. M., Picton, C., Shaw, D. and Bevan, Y.: Subpopulations of 5-HT1D recognition sites in guinea-pig, rabbit, dog and human cortex. The Second IUPHAR Satellite Meeting on Serotonin, Basel, Switzerland, Jul. 11–13, 1990, Abstract # P-30.

Miller, J., and R. N. Germain. Efficient cell surface expression of class II MHC molecules in the absence of associated invariant chain. J.Exp.Med. 164:1478–1489, 1986.

Nieuwenhuys, R., Voogd, J. and van Huijzen, C.: The human nervous system: A synopsis and atlas. New York: Springer Verlag, 1988.

Osborne, N. N. and Hamon, M.: Neuronal serotonin. Chichester: John Wiley and Sons, Inc., 1988.

Peroutka, S. J.: Serotonin receptor subtypes: Basic and clinical aspects. New York: Wiley-Liss, Inc., 1991.

Peroutka, S. J. and Snyder, S. H.: Multiple serotonin receptors, differential binding of [$^3$H]5-hydroxytryptamine, [$^3$H]lysergic acid diethylamide and [$^3$H]spiroperidol. Mol. Pharmacol. 16:687–699, 1979.

Pritchett, D. B., Bach, A. W. J., Wozny, M., Taleb, O., Dal Toso, R., Shih, J. and Seeburg, P. H.: Structure and functional expression of cloned rat serotonin 5-HT2 receptor. EMBO J. 7:4135–4140, 1988.

Rapport, M. M., Green, A. A. and Page, I. H.: Purification of the substance which is responsible for vasoconstrictor activity of serum. Fed. Proc. 6:184, 1947.

Rapport, M. M.: Serum vasoconstrictor (serotonin) V. Presence of creatinine in the complex. A proposed structure of the vasoconstrictor principle. J. Biol. Chem. 180:961–969, 1949.

Sanger, S. DNA sequencing with chain-terminating inhibitors. Proc.Natl.Acad.Sci.USA 74:5463–5467, 1977.

Sanders-Bush, E.: The Serotonin Receptors. Clifton, N.J.: Humana Press, 1988.

Southern, E. M. Detection of specific sequences among DNA fragments separated by gel electrophoresis. J.Mol.Biol. 98:503–505, 1975.

Wilkinson, L. O. and Dourish, C. T.: Serotonin and animal behavior. In: Serotonin receptor subtypes: Basic and clinical aspects. (ed. Peroutka, S. J.) New York:Wiley-Liss, Inc., pgs. 147–210, 1991.

Yamamura, H. I., Enna, S. J. and Kuhar, M. J.: Neurotransmitter receptor binding. New York: Raven Press, 1985.

---

What is claimed is:

1. A process for identifying a chemical compound which specifically binds to a human 5-$HT_{1E}$ receptor, which comprises contacting nonneuronal cells expressing on their cell surface the human 5-$HT_{1E}$ receptor, wherein the human 5-$HT_{1E}$ receptor has the amino acid sequence shown in FIG. 1 (SEQ ID NO: 2), with the chemical compound under conditions suitable for binding, and detecting specific binding of the chemical compound to the human 5-$HT_{1E}$ receptor.

2. A process for identifying a chemical compound which specifically binds to a human 5-$HT_{1E}$ receptor, which comprises contacting a membrane fraction from a cell extract of nonneuronal cells expressing on their cell surface the human 5-$HT_{1E}$ receptor, wherein the human 5-$HT_{1E}$ receptor has the amino acid sequence shown in FIG. 1 (SEQ ID NO: 2), with the chemical compound under conditions suitable for binding, and detecting specific binding of the chemical compound to the human 5-$HT_{1E}$ receptor.

3. A process involving competitive binding for identifying a chemical compound which specifically binds to a human 5-$HT_{1E}$ receptor which comprises separately contacting nonneuronal cells expressing on their cell surface the human 5-$HT_{1E}$ receptor, wherein the human 5-$HT_{1E}$ receptor has the amino acid sequence shown in FIG. 1 (SEQ ID NO: 2), with both the chemical compound and a second chemical compound known to bind to the receptor, and with only the second chemical compound, under conditions suitable for binding, and detecting specific binding of the chemical compound to the human 5-$HT_{1E}$ receptor, a decrease in the binding of the second chemical compound to the human 5-$HT_{1E}$ receptor in the presence of the chemical compound indicating that the chemical compound binds to the human 5-$HT_{1E}$ receptor.

4. A process involving competitive binding for identifying a chemical compound which specifically binds to a human 5-$HT_{1E}$ receptor which comprises separately contacting a membrane fraction from a cell extract of nonneuronal cells expressing on their cell surface the human 5-$HT_{1E}$ receptor, wherein the human 5-$HT_{1E}$ receptor has the amino acid sequence shown in FIG. 1 (SEQ ID NO: 2), with both the chemical compound and a second chemical compound known to bind to the receptor, and with only the second chemical compound, under conditions suitable for binding, and detecting specific binding of the chemical compound to the human 5-$HT_{1E}$ receptor, a decrease in the binding of the second chemical compound to the human 5-$HT_{1E}$ receptor in the presence of the chemical compound indicating that the chemical compound binds to the human 5-$HT_{1E}$ receptor.

5. A process for determining whether a chemical compound specifically binds to and activates a human 5-$HT_{1E}$ receptor, which comprises contacting nonneuronal cells producing cAMP and expressing on their cell surface the human 5-$HT_{1E}$ receptor, wherein the human 5-$HT_{1E}$ receptor has the amino acid sequence shown in FIG. 1 (SEQ ID NO: 2), with the chemical compound under conditions suitable for activation of the human 5-$HT_{1E}$ receptor, and measuring cAMP formation in the presence and in the absence of the chemical compound, decrease in cAMP formation in the presence of the chemical compound indicating that the chemical compound activates the human 5-$HT_{1E}$ receptor.

6. A process for determining whether a chemical compound specifically binds to and activates a human 5-$HT_{1E}$ receptor, which comprises contacting a membrane fraction from a cell extract of nonneuronal cells producing cAMP and expressing on their cell surface the human 5-$HT_{1E}$ receptor, wherein the human 5-$HT_{1E}$ receptor has the amino acid sequence shown in FIG. 1 (SEQ ID NO: 2), with the chemical compound under conditions suitable for activation of the human 5-$HT_{1E}$ receptor, and measuring the cAMP formation in the presence and in the absence of the chemical compound, a decrease in cAMP formation in the presence of the chemical compound indicating that the chemical compound activates the human 5-$HT_{1E}$ receptor.

7. A process for determining whether a chemical compound specifically binds to and inhibits activation of a human 5-$HT_{1E}$ receptor, which comprises separately contacting nonneuronal cells producing cAMP and expressing on their cell surface the human 5-$HT_{1E}$ receptor, wherein the human 5-$HT_{1E}$ receptor has the amino acid sequence shown in FIG. 1 (SEQ ID NO: 2), with both the chemical compound and a second chemical compound known to activate the human 5-$HT_{1E}$ receptor, and with only the second chemical compound, under conditions suitable for activation of the human 5-$HT_{1E}$ receptor, and measuring cAMP formation in the presence of only the second chemical compound and in the presence of both the second chemical compound and the chemical compound, a smaller decrease in cAMP formation in the presence of both the chemical compound and the second chemical compound than in the presence of only the second chemical compound indicating that the chemical compound inhibits activation of the human 5-$HT_{1E}$ receptor.

8. A process for determining whether a chemical compound specifically binds to and inhibits activation of a human 5-HT$_{1E}$ receptor, which comprises separately contacting a membrane fraction from a cell extract of nonneuronal cells producing cAMP and expressing on their cell surface the human 5-HT$_{1E}$ receptor, wherein the human 5-HT$_{1E}$ receptor has the amino acid sequence shown in FIG. 1 (SEQ ID NO: 2), with both the chemical compound and a second chemical compound known to activate the human 5-HT$_{1E}$ receptor, and with only the second chemical compound, under conditions suitable for activation of the human 5-HT$_{1E}$ receptor, and measuring cAMP formation in the presence of only the second chemical compound and in the presence of both the second chemical compound and the chemical compound, a smaller decrease in cAMP formation in the presence of both the chemical compound and the second chemical compound than in the presence of only the second chemical compound indicating that the chemical compound inhibits activation of the human 5-HT$_{1E}$ receptor.

9. The process of any one of claims 1, 2, 3, 4, 5, 6, 7 or 8, wherein the nonneuronal cell is a mammalian cell.

10. The process of claim 9, wherein the mammalian cell is an LTk$^-$ cell or a Y1 cell.

* * * * *

UNITED STATES PATENT AND TRADEMARK OFFICE
CERTIFICATE OF CORRECTION

PATENT NO. : 5,786,155
DATED : July 28, 1998
INVENTOR(S) : Richard L. Weinshank, Theresa A. Branchek, Paul R. Hartig It is certified that error appears in the above-identified patent and that said Letters Patent is hereby corrected as shown below:

column 1, line 52: "5-HT$_{18}$" should read --5-HT$_{1B}$--
        line 52: "5-HT$_{10}$" should read --5-HT$_{1D}$--
        line 65: "5-HT$_{10}$" should read --5-HT$_{1D}$--
column 7, line 47: "$^5$-HT$_{1E}$" should read --5-HT$_{1E}$--
        line 50: "1-HT$_{1E}$" should read --5-HT$_{1E}$--
column 8, line 41: "$^5$-HT$_{1E}$" should read --5-HT$_{1E}$--
column 9, line 64: "Y-5-HT$_E$" should read --Y-5-HT$_{1E}$--
column 13, line 8: "tb" should read --to--
column 18, line 45: "5-HT$_1$" should read --5-HT$_{1E}$--
column 19, line 53: "5' ACCACGCGGCCAAGAGCCTTTACCA 3'"
    should read --5' TACCACGCGGCCAAGAGCCTTTACCA 3'--
column 20, line 2: "5HT12E" should read --5-HT$_{1E}$--
column 23, line 25, table 1: "variou" should read --various--
        line 32, table 1: "5-NT" should read --5-HT--
        line 34, table 1: "Ergonavine" should read --Ergonovine--
        line 35, table 1: "Methylerogavine" should read --Methylerogovine--
        line 36, table 1: "a-Methyl-5-NT" should read --a-Methyl-5-HT--
        line 42, table 1: "2-Methyl-5-NT" should read --2-Methyl-5-HT--
        line 45, table 1: "DCl" should read --DOI--
        line 48, table 1: "Rauaolacine" should read --Rauwolscine--
        line 50, table 1: "TFNPP" should read --TFMPP--
column 24, line 28: "$^5$HT$_{1C}$" should read --5-HT$_{1C}$--

UNITED STATES PATENT AND TRADEMARK OFFICE
CERTIFICATE OF CORRECTION

PATENT NO. : 5,786,155
DATED : July 28, 1998
INVENTOR(S) : Richard L. Weinshank, Theresa A. Branchek, Paul R. Hartig It is certified that error appears in the above-identified patent and that said Letters Patent is hereby corrected as shown below:

In the claims:

claim 5, column 52, line 32: "decrease" should read --a decrease--

Signed and Sealed this

Twenty-third Day of February, 1999

Attest:

Q. TODD DICKINSON

*Attesting Officer*   *Acting Commissioner of Patents and Trademarks*